(12) United States Patent
Cheung

(10) Patent No.: US 9,416,422 B2
(45) Date of Patent: Aug. 16, 2016

(54) METHODS FOR DETECTING MINIMUM RESIDUAL DISEASE

(75) Inventor: Nai-Kong Cheung, Purchase, NY (US)

(73) Assignee: Sloan-Kettering Institute for Cancer Research, New York, NY (US)

(*) Notice: Subject to any disclaimer, the term of this patent is extended or adjusted under 35 U.S.C. 154(b) by 1634 days.

(21) Appl. No.: 11/884,602

(22) PCT Filed: Feb. 17, 2006

(86) PCT No.: PCT/US2006/005591
§ 371 (c)(1),
(2), (4) Date: May 2, 2008

(87) PCT Pub. No.: WO2006/089091
PCT Pub. Date: Aug. 24, 2006

(65) Prior Publication Data
US 2009/0023142 A1    Jan. 22, 2009

Related U.S. Application Data

(60) Provisional application No. 60/654,118, filed on Feb. 18, 2005, provisional application No. 60/672,246, filed on Apr. 18, 2005.

(51) Int. Cl.
*C12Q 1/68* (2006.01)

(52) U.S. Cl.
CPC ........ *C12Q 1/6886* (2013.01); *C12Q 2600/106* (2013.01); *C12Q 2600/118* (2013.01)

(58) Field of Classification Search
None
See application file for complete search history.

(56) References Cited

U.S. PATENT DOCUMENTS

2004/0115688 A1    6/2004    Cheung et al.

FOREIGN PATENT DOCUMENTS

WO    WO 02092767 A2 *  11/2002

OTHER PUBLICATIONS

Sugiyama et al. Wilm's tumor gene WT1: Its oncogenic function and clinical application. International Journal of Hematology, vol. 73, pp. 177-187, 2001.*
Howe et al. Real-time quantitative reverse transcription-PCR for cyclin D1 mRNA in blood, marrow, and tissue specimens for diagnosis of mantle cell lymphoma. Clinical Chemistry, vol. 50, pp. 80-87, published online Nov. 21, 2003.*
van der Velden et al. Detection of minimal residual disease in hematologic malignancies by real-time quantitative PCR: principles, approaches, and laboratory aspects. Leukemia, vol. 17, pp. 1013-1034, 2003.*
Seykora et al. Gene expression profiling of melanocytic lesions. The American Journal of Dermatopathology, vol. 25, No. 1, pp. 6-11, Feb. 2003.*
Wai et al. Expression analysis of pediaatric solid tumor cell lines using oligonucleotide microarrays. International Journal of Oncology, vol. 20, No. 3, pp. 441-451, Mar. 2002.*
Bartkova et al. Cyclin D1 protein expression and function in human breast cancer. International Journal of Cancer, vol. 57, No. 3, pp. 353-361, 1994.*
Taback et al. Detection of occult metastatic breast cancer cells in blood by a multimolecular marker assay: Correlation with clinical stage of disease. Cancer Research, vol. 61, pp. 8845-8850, Dec. 2001.*
Molenaar et al. Rearrangements and increased expression of cyclin D1 (CCND1) in neuroblastoma. Genes, Chromosomes & Cancer, vol. 36, pp. 242-249, 2003.*
EST Profile for Hs.435609, printed from http://www.ncbi.nlm.nih.gov/UniGene/ESTProfileViewer.cgi?uglist=Hs.435609, printed as pp. 1/3-3/3 on Sep. 29, 2014.*
Kagedal et al. Pterin-dependent tyrosine hydroxylase mRNA is not expressed in human melanocytes or melanoma cells. Pigment Cell Research, vol. 17, pp. 346-351, 2004.*
Wang et al. Expression of protein gene product 9.5 and tyrosine hydroxylase in childhood small round cell tumors. Clincal Cancer Research, vol. 6, pp. 551-558, 2000.*
Cheung et al. Early molecular response of marrow disease to biologic therapy is highly prognostic in neuroblastoma. Journal of Clinical Oncology, vol. 21, No. 20, pp. 3853-3858, Oct. 2003.*
Cheung, et al., "Cyclin D1, a Novel Molecular Marker of Minimal Residual Disease, in Metastatic Neuroblastoma", Journal of Molecular Diagnostics, vol. 9. No. 2, Apr. 2007, pp. 237-241.
Cheung, et al., Novel Markers of Subclinical Disease for Ewing Family Tumors from Gene Expression Profiling, Clin Cancer Res 2007; 13(23) Dec. 1, 2007, pp. 6978-6983.
Cheung Iy et al. "Exploiting gene expression profiling to identify novel minimal residual disease markers of neuroblastoma." Clin Cancer Res. Nov. 1, 2008;14(21):7020-7.
Ogawa H et al. "WT1 gene transcript assay for relapse in acute leukemia after transplantation." Leuk Lymphoma. Sep. 2004;45(9):1747-53.

* cited by examiner

*Primary Examiner* — Jennifer Dunston
(74) *Attorney, Agent, or Firm* — Heslin Rothenberg Farley and Mesiti, PC

(57) ABSTRACT

The present invention features methods and compositions for identifying markers of minimum residual disease (MRD), as well as markers of metastatic cells. The present invention further provides methods for detecting MRD and metastatic cell in a subject.

11 Claims, 5 Drawing Sheets

METHODS FOR DETECTING MINIMUM RESIDUAL DISEASE

This application is the U.S. national phase application, pursuant to 35 U.S.C. §371, of PCT international application Ser. No. PCT/US2006/005591, filed Feb. 17, 2006, designating the United States and published in English on Aug. 24, 2006 as publication WO 2006/089091 A2, which claims priority to U.S. provisional application Ser. No. 60/654,118, filed Feb. 18, 2005, and 60/672,246, filed Apr. 18, 2005. The entire contents of the aforementioned patent applications are incorporated herein by this reference.

RELATED APPLICATIONS/PATENTS & INCORPORATION BY REFERENCE

This application claims priority to U.S. Provisional Application Ser. No. 60/654,118, filed Feb. 18, 2005 and to U.S. Provisional Application Ser. No. 60/672,246, filed Apr. 18, 2005, the contents of which are incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), are hereby expressly incorporated by reference.

BACKGROUND OF THE INVENTION

The study of circulating tumor cells can yield important biologic and clinical information. Yet, it has been limited by the paucity of specific and sensitive markers. Pre-genomic approaches rely on known tumor-associated phenotypes or genetic aberrations. For example, cytokeratins were widely used as markers of circulating breast cancer cells (Pantel, K., et al. 2004 *Nat Rev Cancer* 4:448-56).

Molecular-based methods for the detection of cancer have greatly energized the cancer community because of their promise of exquisite specificity and sensitivity (Sidransky, D. 1997 *Science* 278:1054-9). Nevertheless, measuring DNA from tumor cells by PCR has largely been restricted to known tissue-specific antigens and tumor-associated mutations in oncogenes or in tumor suppressors. RT-PCR has also been used to detect tumor-specific transcripts, but again mRNA sequences were primarily based on known aberrations. Most importantly, it is not uncommon for these so called "tumor-specific" transcripts to be found in normal hematopoietic cells.

Sophisticated use of chemotherapy, surgery, and/or radiation therapy can reduce cancers to near complete remission. However, cancer cure remains elusive, the major hurdle being minimal residual disease (MRD) below the detection limit of conventional radiographic or histopathological tools. Since the current eligibility criteria of most clinical trials require evidence of gross disease, a tumor will not be treated until it is measurable and symptomatic. This "killing paradigm" maybe undesirable for several reasons (Schipper, H., et al. 1995 *J Clin Oncol* 13(4):801-7). First, the Goldie-Coldman hypothesis predicts that bigger tumors have higher likelihoods of mutations and resistance (Goldie, J. H., et al. 1989 Devita H R, ed. Cancer. Principles and Practice of Oncology. $3^{rd}$ ed. Philadelphia, Pa.: JP Lippincott. 1-12). Second, visible tumors acquire additional barriers to drug delivery (e.g. sub-optimal tumor pressure, vasculature and oxygenation) (Semanza, G. L. 2003 *Nat Rev Cancer* 3(10):721-32; Jain, R. K. 2005 *Science* 307(5706):58-62). Third, a patient with measurable tumors is physically and/or mentally compromised, and is less likely to tolerate treatment side effects. An alternative strategy of "regulatory control" has been proposed (Schipper, H., et al. 1995 *J Clin Oncol* 13(4):801-7). This treatment paradigm is particularly relevant to today's cancer therapeutics. While novel agents such as angiogenesis inhibitors, growth modulators or vaccines may not achieve rapid tumor shrinkage, they may nevertheless be effective in controlling MRD, such that patients can "live with cancer".

Targeting subclinical disease is particularly pertinent to high risk neuroblastoma (NB), a pediatric cancer which poses enormous clinical challenges because of its tumor bulk, the extent of metastatic spread, and its orphan disease status. Although most patients achieve near complete remission, they typically relapse because of refractory MRD. Adjuvant therapies such as stem cell transplantation and immunotherapy are employed, but the ability to measure MRD accurately is crucial to determine their anti-tumor effect, to identify the optimal timing for stem cell collection, and to provide early indications of treatment failure.

The detection of MRD using molecular-based methods shows great promise because of its exquisite specificity and sensitivity (Sidransky, D. 1997 *Science* 278(5340): 1054-9). One such technique is quantitative reverse transcription-polymerase chain reaction (qRT-PCR) to measure tumor transcripts. The clinical utility of tyrosine hydroxylase (TH), an established NB marker, has been extensively described (Naito, H., et al. 1991 *Eur J Cancer* 27:762-765; Miyajima, Y., et al. 1995 *Cancer* 75:2757-2761). GD2 synthase ($\beta$1,4-N-acetylgalactosaminyltransferase, GD2/GM2 synthase, GalNacT) is also a useful MRD marker in the bone marrow (BM) and peripheral blood (PB) among high risk NB patients (Cheung, I. Y., et al. 2001 *Clin Cancer Res* 7(6):1698-705; Cheung, I. Y., et al. 2003 *J Clin Oncol* 21(6):1087-93).

In order to prevent relapse, adjuvant therapy such as autologous marrow or peripheral blood stem cell transplantation and immunotherapy are often employed. It stands to reason that accurate quantitation of MRD can identify the optimal timing for stem cell collection and evaluate the efficacy of adjuvant therapies, permitting the monitoring of tumor activity previously undetectable by standard histologic and radiographic techniques. In children, where late effects of prolonged treatment are of grave concern, specific and sensitive markers of MRD may provide objective endpoints for terminating cytotoxic therapy.

Thus, improved methods for the identification of patients having MRD are desired for the diagnosis and treatment of cancer patients.

SUMMARY OF THE INVENTION

In one aspect, the invention is directed to a method for identifying a marker of minimum residual disease (MRD), the method comprising the steps of:
  a) measuring the mRNA expression level of a gene in a tumor;

b) measuring the mRNA expression level of the gene in the bone marrow or peripheral blood from normal subjects or subject cured of their tumor; and c) comparing the mRNA expression level in (a) to the mRNA level in (b), wherein a gene with an (a)/(b) ratio of at least about 20 for marrow or at least about 5 for blood is identified as a marker of MRD, thereby identifying a marker of minimum residual disease (MRD).

In another aspect, the invention is directed to a method for identifying a marker of circulating tumor cells in the blood, the method comprising the steps of:

a) measuring the mRNA expression level of a gene in a tumor;

b) measuring the mRNA expression level of the gene in the peripheral blood; and c) comparing the mRNA expression level in (a) to the mRNA level in (b), wherein a gene with an (a)/(b) ratio of at least about 5 is identified as a marker of circulating tumor cells in the blood, thereby identifying a marker of circulating tumor cells in the blood.

In yet another aspect, the invention is directed to a method for identifying a marker of circulating tumor cells in the marrow, the method comprising the steps of:

a) measuring the mRNA expression level of a gene in a tumor;

b) measuring the mRNA expression level of the gene in the bone marrow; and c) comparing the mRNA expression level in (a) to the mRNA level in (b), wherein a gene with an (a)/(b) ratio of at least about 5 is identified as a marker of circulating tumor cells in the marrow, thereby identifying a marker of circulating tumor cells in the marrow.

In specific embodiments, the (a)/(b) ratio for blood is at least about 10, at least about 20 or at least about 30.

In specific embodiments, the (a)/(b) ratio for marrow is at least about 30.

In specific embodiments, the p value for the gene identified is less than 0.05.

In performing methods of the invention, the mRNA expression level can be measured using a biochip, such as an Affymetrix U-95 or U133 chip. Methods of the invention may further comprise obtaining the biochip. The mRNA expression level can also be measured using quantitative RT-PCR.

In other embodiments, methods of the invention may further comprise the steps of:

d) measuring the mRNA expression level of the gene in a cell line derived from the same cell type as the tumor;

e) comparing the mRNA expression level in (d) to the mRNA level in (b), wherein a gene with an (d)/(b) ratio of ≥10 is further identified as a marker of MRD.

In specific embodiments, the (d)/(b) ratio is ≥50, and/or the p value for the gene identified is less than 0.05.

In performing methods of the invention, the tumor can be but is not limited to a neuroblastoma, breast cancer, Ewing's sarcoma, colon cancer, liver cancer, brain cancer, prostate cancer, leukemia, lymphoma, pancreatic cancer, skin cancer, ovarian cancer, uterine cancer, bone cancer, lung cancer, squamous cell lung cancer (SCC), non-small cell lung cancer (NSCLC), small cell lung cancer (SCLC), osteosarcoma, thyroid cancer, stomach cancer, melanoma, clear cell sarcoma, rhabdomyosarcoma, soft tissue sarcoma, and bladder cancer.

In yet another aspect, the invention is directed to a method of identifying a subject with MRD comprising measuring the mRNA expression level of at least one marker of MRD in a peripheral blood or bone marrow sample obtained from a subject in remission from a tumor, wherein expression of the MRD marker in the peripheral blood or bone marrow sample identifies the subject as having MRD. In specific embodiments, the expression level of the MRD marker is at least 2 standard deviations ("SD") above the mean expression level of the MRD marker in normal peripheral blood or bone marrow samples.

MRD markers of the invention can be but are not limited to CCND1, STMN2, CHGB, MAB21L1, DPYSL3, PGP9.5, KIF5C, GAP43, CRMP1, LICAM, SCG2, ISL1, PHOX2B, RTN1, NP25, MAOA, AF1Q, NPY, RBP1, DDC, RGS5, PFN2, TH, ELAVL4, KIF21A, MAP2, KIF1A, MEG3, TACC, PCSK1N, GABRB3, GRIA2, SOX11, IDAX, CNTFR and combinations thereof and preferably, the tumor is a neuroblastoma.

In yet another aspect, the invention is directed to a method of identifying a metastatic tumor cell in a subject comprising detecting mRNA expression of at least one marker of MRD in a peripheral blood or bone marrow sample obtained from a subject, wherein expression of the MRD marker in the peripheral blood or bone marrow sample identifies the subject as having a metastatic tumor cell.

In yet another aspect, the invention is directed to a method for identifying a single tumor cell in the blood of a subject comprising detecting mRNA expression of at least one marker of MRD in a blood sample obtained from the subject, wherein expression of the MRD marker in the blood sample of the subject identifies a single tumor cell in the blood of the subject.

In yet another aspect, the invention is directed to a method for identifying a single tumor cell in the bone marrow of a subject comprising detecting mRNA expression of at least one marker of MRD in a bone marrow sample obtained from the subject, wherein expression of the MRD marker in the bone marrow sample of the subject identifies a single tumor cell in the bone marrow of the subject.

MRD markers of the invention can be but are not limited to FAP, OSF-2, THBS2, MYO1B, LUM, FAT, LOX, CCND1, THBS2, IGSF4, LOC92689, SEPT10, ME1 and combinations thereof and preferably, the tumor is an osteosarcoma.

MRD markers of the invention can be but are not limited to MGP, FXYD3, IGFBP5, CDH1, TACSTD2, TACSTD1, AGR2, PBX1, CRABP2, KRT7, SCNN1A, CLDN3, RAI3, MYO6, CCND1 and combinations thereof and preferably, the tumor is a breast cancer.

MRD markers of the invention can be but are not limited to ASCL1, SCNN1A, GRP, ISL1, NP25, CHGA, INSM1, SCG2, DDC, IGSF4, CRMP1, OSF-2 and combinations thereof and preferably, the tumor is a small cell lung cancer ("SCLC").

MRD markers of the invention can be but are not limited to OSF-2, TFAP2A, SOX2, S100A2 and combinations thereof and preferably, the tumor is a squamous cell lung cancer ("SCC").

MRD markers of the invention can be but are not limited to FXYD3, MGP, ALDH1A3, CDH1, TACSTD2, HOXB13, IGFBP5, TSPAN-13, AGR2, PSMAL/GCP III, FOLH1, TACSTD1 and combinations thereof and preferably, the tumor is a prostate cancer.

MRD markers of the invention can be but are not limited to CCND1, PKP1, NKX2-2, STEAP, TM4SF10, CSPG5, FLRT2, MAPT, WNT5A, FATJ, NPTXR, SEPT10, MAPT, PTPN13, PBX1, MGC29643 and combinations thereof and preferably, the tumor is a Ewing's Sarcoma.

MRD markers of the invention can be but are not limited to FABP1, FXYD3, TACSTD1, CDH1, CEACAM5, kindling 1, LUM, KRT20, AGR2, RAI3, MGP, LGALS4, CLDN3, MET, SCNN1A, TM4SF6, THBS1, CCL20, IGFBP5, PLOD2, PHLDA2, KRT23 and combinations thereof and preferably, the tumor is a colon cancer.

MRD markers of the invention can be but are not limited to SFTPB, SFTPA2, TACSTD2, AGR2, MGP, TACSTD1, TITF1, SCNN1A and combinations thereof and preferably, the tumor is a non-small cell lung carcinoma (NSCLC).

MRD markers of the invention can be but are not limited to MYO10, TFAP2A, ERBB3, PLP1, CCND1 and combinations thereof and preferably, the tumor is a melanoma.

MRD markers of the invention can be but are not limited to CAPN6, LUM, MEG3, PEG3, OSF-2, ACTC, TM4SF10, MYOD1, MET, RYR1, SEPT10, ABAT and combinations thereof and preferably, the tumor is a rhabdomyosarcoma.

MRD markers of the invention can be but are not limited to TUSC3, CPE, PDZRN3, PTGIS, PMX1, SEPT10, PWIST and combinations thereof and preferably, the tumor is a soft tissue sarcoma.

Methods of the invention can further comprise administering treatment to the subject identified as having MRD or a tumor (e.g., a metastatic tumor). The treatment can be, for example, chemotherapy, radiation, immunotherapy, and targeted therapy using small molecules (e.g., anti-angiogenic agents).

Other features and advantages of the invention will be apparent from the following detailed description and claims.

DETAILED DESCRIPTION OF THE INVENTION

Figure 1A:
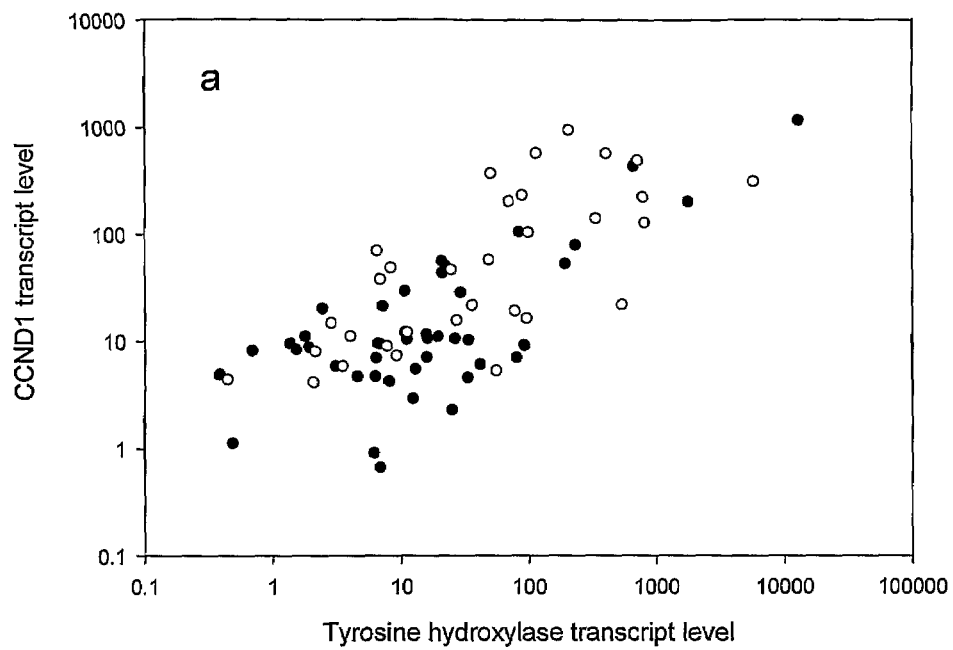
FIG. 1 shows, A, CCND1 versus tyrosine hydroxylase transcript levels of 260 marrow samples plotted on log scales. Solid circles: pre-treatment samples (n=136, correlation coefficient, R=0.91). Open circles: post-treatment samples (n=124, R=0.30); B, CCND1 versus GD2 synthase transcript levels. Solid circles: pre-treatment samples (R=0.97). Open circles: post-treatment samples (R=0.75).

The present invention is based, at least in part, on the discovery of genes which are markers of minimum residual disease (MRD). The markers described herein may be used to identify subjects with MRD, as well as isolated cells in the blood or bone marrow, including metastatic cells, of subjects with tumors and/or MRD.

As used herein, the terms "minimum residual disease" and "MRD" include a situation or condition where, by standard radiographic and histologic criteria, there is no evidence of disease in a subject, but where the subject in fact has residual tumor cells in the blood or bone marrow which are capable of growing into tumors. Typically, MRD occurs after the use of chemotherapy, surgery and/or radiation therapy. Standard radiographic and histologic detection methods may include, for example, imaging tests (X-rays, ultrasound, MRI), blood or immunochemical tests for known tumor markers, testing biopsies or cytology specimens for known tumor markers to assess, for example, the number of tumor cells present or the relative rarity of such cells.

Markers of MRD include the following markers, and combinations thereof, known in the art, the sequences of which can be obtained for example, at their respective GENBANK accession numbers: AF1Q (AK056089); CCND1 (NM 053056); CHUB (NM_001819); CNTFR (NM_147164); CRMP1 (NM001014809); DDC (NM_000790); DPYSL3 (NM 001387): ELAVL4 (NM 204830); GABRB3 (NM 000814); GAP43 (NM 002045); GRIA2 (NM 000826); IDAX (AK127778); ISL1 (NM_002202); KIFTA (NM 008440); KIF21A (AK124704); KIF5C (NM 008449) L1CAM (NM 000425); MAB21L1 (NM 005584); MAOA (NM 000240); MAP2 (NM_002374); MEG3 (NR 002766); NP25 (AB031291); NPY (NM_00905); PCSK1N (NM 013271); PFN2 (NM_053024); PGP9.5 (D10699); PHOX2B (NM 003924); RBP1 (S66427); RGS5 (NM_003617); RTNI (DQ355431); SCG2 (NM_009129); SOX11 (NM 003108); STMN2 (NM_007029); TACC (NM 177089); FAP (NM_000038); OSF-2 (AK134925); THBS2 (NM 003247); MYO1B (NM 012223); LUM (NM 008524); FAT (XM585004); LOX (NM 010728); IGSF4 (NM 014333); LOC92689 (NM_138389); SEPT10 (NM 144710); ME1 (NM_002395); MGP (NM 000900); FXYD3 (NM 00591); IGFBP5 (NM 000599); CDH1 (NM 004360); TACSTD2 (NM_002353); TACSTD1 (NM 002354); AGR2 (NM 006408); PBX1 (XM925069); CRABP2 (NM 001878); KRT7 (NM_005556); SCNN1A (NM_001038); CLDN3 (NM_001306); RAI3 (BC086372); MYO6 (NM 004999); ASCL1 (NM_004316); GRP (NM_002091) ISL1 (NM 002202); CHGA (NM 001275); INSM1 (NM 002196); SCG2 (NM 009129); DDC (NM_000790); IGSF4 (NM 014333); TFAP2A (NM 003220); SOX2 (NM 003106); S100A2 (NM_005978) FXYD3 (NM 005971); MGP (NM 000900); ALDH1A3 (AK124965); CDH1 (NM_004360); HOXB13 (NM 006361); TSPAN-13 (NM 014399); PSMAL/ GCP III (NM 153696); FOLH1 (NM_004476); PKP1 (NM 001005337); NKX2-2 (NM 010919); STEAP (NM 012449); TM4SF10 (BX842568); CSPG5 (NM 006574); FLRT2 (NM 013231); MAPT (NM 016835); WNT5A (NM 003392); FAT-J(AY356402); NPTXR (NM 014293); PTPN13 (NM 080683); PBX1 (XM925069); MGC29643 (BC017318); FABP1 (NM_001443); FXYD3 (NM 005971); CEACAMS (NM 001024912); KRT20 (NM 019010); LGALS4 (NM 006149); CLDN3 (NM 001306); MET (NM_000245); TM4SF6 (NM 003270); THBS1 (NM_003246); CCL20 (NM 004591); IGFBP5 (NM 000599); PLOD2 (NM 182943); PHLDA2 (NM_003311); KRT23 (NM 015515); SFTPB (NM 000542); SFTPA2 (NM_006926); TITF1 (NM 003317); MYO10 (NM 012334); TFAP2A (NM_001032280); ERBB3 (NM 001982); PLP1 (NM 000533); CAPN6 (NM_014289); PEG3 (NM 006210); ACTC (NM 005159); TM4SF10 (BX842568); MYOD1 (NM 002478); RYR1 (NM_000540); ABAT (NM 000663); TUSC3 (NM_178234); CPE (NM 001873); PDZRN3 (NM_015009); PTGIS (NM 000961) and PMX1 (BQ259022).

Preferably, markers of MRD identified according to the methods provided herein have a p value of less than 0.05, as determined by the student t test after Bonferroni correction for multiple comparisons (Bland, J. M., et al. (1995) BMJ 310:170-171).

Isolated Nucleic Acid Molecules

One aspect of the invention pertains to the use of isolated nucleic acid molecules comprising the markers described herein, including nucleic acid fragments sufficient for use as hybridization probes to identify nucleic acid molecules (e.g., mRNA) that encode the markers described herein and fragments for use as PCR primers for the amplification of the markers. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one that is separated from other nucleic acid molecules which are present in the natural source of the nucleic acid. An "isolated" nucleic acid is free of sequences that naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule used in the methods of the present invention can be isolated using standard molecular biology techniques and the sequence information provided herein. Using all or a portion of the nucleic acid sequences of the markers (see the GENBANK Accession numbers provided herein) as a hybridization probe, marker nucleic acid molecules can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of a marker can be isolated by the polymerase chain reaction (PCR) using synthetic oligonucleotide primers designed based upon the known marker sequences.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to marker nucleotide sequences can be prepared by standard synthetic techniques, e.g., using an automated DNA synthesizer.

In another embodiment, an isolated nucleic acid molecule used in the methods of the invention comprises a marker nucleic acid molecule which is a complement of the known marker nucleotide sequence, or a portion of these nucleotide sequences. A nucleic acid molecule which is complementary to a nucleotide sequence is one which is sufficiently complementary to the nucleotide sequence such that it can hybridize to the nucleotide sequence.

In still another embodiment, an isolated nucleic acid molecule used in the methods of the present invention comprises a nucleotide sequence which is at least about 75%, 85%, 95% or more homologous (or identical) to the entire length of the marker nucleotide sequence, or a portion of this nucleotide sequence.

Moreover, the nucleic acid molecule used in the methods of the invention can comprise only a portion of the nucleic acid sequence of a marker, for example a fragment which can be used as a probe or primer or a fragment encoding a biologically active portion of a marker protein. The nucleotide sequence described in the GENBANK records described herein allows for the generation of probes and primers designed for use in identifying and/or cloning related isoforms, as well as homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of a marker nucleic acid sequence, or of a naturally occurring allelic variant or mutant.

Probes based on the marker nucleotide sequences can be used to detect transcripts encoding related isoforms. The probe can further include a label group attached thereto, e.g., the label group can be a radioisotope, a fluorescent compound, an enzyme, or an enzyme co-factor. Such probes can be used as a part of a diagnostic test kit for identifying tumor cells which express or misexpress a marker gene, such as by measuring a level of a marker nucleic acid in a sample of cells from a subject e.g., detecting marker mRNA levels.

The invention further encompasses the use of nucleic acid molecules that differ from the nucleotide sequences shown in the GENBANK records, due to degeneracy of the genetic code and thus encode the same marker proteins as those encoded by the known nucleotide sequence.

In addition to the marker nucleotide sequences shown in the GenBank records, it will be appreciated by those skilled in the art that DNA sequence polymorphisms that lead to changes in the amino acid sequences of the marker proteins may exist within a population. Such genetic polymorphism in the marker genes may exist among individuals within a population due to natural allelic variation. As used herein, the terms "gene" and "recombinant gene" refer to nucleic acid molecules comprising an open reading frame encoding a marker protein. Such natural allelic variations can typically result in 1-5% variance in the nucleotide sequence of a marker gene. Any and all such nucleotide variations and resulting amino acid polymorphisms in marker genes that are the result of natural allelic variation and that do not alter the functional activity of a marker protein are intended to be within the scope of the invention.

Nucleic acid molecules corresponding to natural allelic variants and homologues of the markers of the invention can be isolated based on their homology to the known nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequences validated in public domains including, but not limited to, GENBANK. Preferably, the molecule hybridizes under highly stringent conditions. As used herein, the term "hybridizes under stringent conditions" is intended to describe conditions for hybridization and washing under which nucleotide sequences at least 60%, 85%, or 95% homologous to each other typically remain hybridized to each other. Hybridization conditions are known to those skilled in the art and can be found in Current Protocols in Molecular Biology, John Wiley & Sons, N.Y., 1991. Moderate hybridization conditions are defined as equivalent to hybridization in 2×sodium chloride/sodium citrate (SSC) at 30 C., followed by a wash in 1×SSC, 0.1% SDS at 50 C. Highly stringent conditions are defined as equivalent to hybridization in 6× sodium chloride/sodium citrate (SSC) at 45 C, followed by a wash in 0.2×SSC, 0.1% SDS at 65. C.

An isolated nucleic acid molecule of the invention that hybridizes under moderate or highly stringent conditions to the marker nucleic acid sequences can correspond to a naturally-occurring nucleic acid molecule. As used herein, a "naturally-occurring" nucleic acid molecule refers to an RNA, cDNA, or DNA molecule having a nucleotide sequence that occurs in nature (e.g., encodes a natural protein).

Test Samples

Samples are collected from subjects who want to establish tumor status, e.g., MRD status and/or metastasis status. The subjects may be patients who have undergone previous cancer treatment, or subjects with tumors presently. Also, subjects may include healthy people who are having a test as part of a routine examination, or to establish baseline levels of the markers. Samples may be collected from people who had been diagnosed with MRD and received treatment to eliminate the residual tumor cells, or who are currently receiving treatment.

The markers can be measured in different types of biological samples. The sample is preferably a biological fluid sample. Blood and bone marrow are the preferred biological samples. Further examples of biological samples useful in this invention include urine, tissue, cells, organs, seminal fluids, cerebrospinal fluid, etc. Because tumor circulate in the blood, blood is a preferred sample source for embodiments of the invention.

Expression Monitoring and Profiling

The presence, level, or absence of marker nucleic acid in a biological sample can be evaluated by obtaining a biological sample from a test subject and contacting the biological sample with a compound or an agent capable of detecting marker nucleic acid (e.g., mRNA) such that the presence of the nucleic acid is detected in the biological sample. The level of expression of the marker gene can be measured in a number of ways, but is preferably measured by measuring marker mRNA. Only living tumor cells carry intact mRNA. In contrast, DNA and proteins are released by normal cells and dead tumor cells. While each cell has only 2 copies of a specific DNA; for each DNA molecule, up to 100,000 molecules of mRNA are present. Hence measuring mRNA is more specific and more sensitive.

The level of mRNA corresponding to a marker gene in a cell can be determined both by in situ and by in vitro formats.

The isolated mRNA can be used in hybridization or amplification assays that include, but are not limited to, Southern or Northern analyses, polymerase chain reaction analyses and probe arrays. One diagnostic method for the detection of mRNA levels involves contacting the isolated mRNA with a nucleic acid molecule (probe) that can hybridize to the mRNA encoded by the gene being detected. The nucleic acid probe can be, for example, a full-length marker nucleic acid, such as the nucleic acids described herein, or a portion thereof, such as an oligonucleotide of at least 7, 15, 30, 50, 100, 250 or 500 nucleotides in length and sufficient to specifically hybridize under stringent conditions to marker mRNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the marker genes.

The level of mRNA in a sample that is encoded by a marker gene can be evaluated with nucleic acid amplification, e.g., by PCR (Mullis (1987) U.S. Pat. No. 4,683,202), ligase chain reaction (Barany, 1991 *Proc. Natl. Acad. Sci. USA* 88:189-193), self sustained sequence replication (Guatelli, et al. 1990 *Proc. Natl. Acad. Sci. USA* 87:1874-1878), transcriptional amplification system (Kwoh, et al. 1989 *Proc. Natl. Acad. Sci. USA* 86:1173-1177), Q-Beta Replicase (Lizardi, et al. 1988 *Bio/Technology* 6:1197), rolling circle replication (Lizardi, et al. U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the marker gene being analyzed.

In another embodiment, the methods herein include further contacting a control sample with a compound or agent capable of detecting marker mRNA, or genomic DNA, and comparing the presence of marker mRNA or genomic DNA in the control sample with the presence of marker mRNA or genomic DNA in the test sample. In still another embodiment, serial analysis of gene expression, as described in U.S. Pat. No. 5,695,937, is used to detect marker transcript levels.

The invention also includes kits for detecting the presence of marker nucleic acids in a biological sample. For example, the kit can include a compound or agent capable of detecting marker protein or mRNA in a biological sample; and a standard. The compound or agent can be packaged in a suitable container. The kit can further comprise instructions for using the kit to detect marker nucleic acids.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also include a buffering agent, a preservative, or a protein stabilizing agent. The kit can also includes components necessary for detecting the detectable agent (e.g., an enzyme, a substrate, a fluorescent dye, or a fluorescence quencher). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

This invention is further illustrated by the following examples which should not be construed as limiting. The contents of all references, patents and published patent applications cited throughout this application, as well as the figures and the sequence listing, are incorporated herein by reference.

EXAMPLES

Example 1

Identification of MRD Markers for Neuroblastoma Cells

Quantitative reverse transcription-polymerase chain reaction (qRT-PCR) is a highly sensitive method to measure tumor transcripts circulating in blood and marrow. It has previously been shown that GD2 synthase (β1,4-N-acetylgalactosaminyltransferase, GM2/GD2 synthase, GalNacT) is a useful marker of MRD (Cheung I Y, Cheung N K: Quantitation of marrow disease in neuroblastoma by real-time reverse transcription-PCR. Clin Cancer Res 7:1698-705, 2001; Cheung I Y, Lo Piccolo M S, Kushner B H, et al: Early molecular response of marrow disease to biologic therapy is highly prognostic in neuroblastoma. J Clin Oncol 21:3853-8, 2003; Cheung I Y, Lo Piccolo M S, Kushner B H, et al: Quantitation of GD2 synthase mRNA by real-time reverse transcriptase polymerase chain reaction: clinical utility in evaluating adjuvant therapy in neuroblastoma. J Clin Oncol 21:1087-93, 2003). Others have described the utility of the tissue specific marker tyrosine hydroxylase (Burchill S A, Bradbury F M, Selby P, et al: Early clinical evaluation of neuroblastoma cell detection by reverse transcriptase-polymerase chain reaction (RT-PCR) for tyrosine hydroxylase mRNA. Eur J Cancer 31A-553-556, 1995; Miyajima Y, Kato K, Numata S I, et al: Detection of neuroblastoma cells in bone marrow and peripheral blood at diagnosis by the reverse transcriptase-polymerase chain reaction for tyrosine hydroxylase mRNA. Cancer 75:2757-2761, 1995; Trager C, Kogner P, Lindskog M, et al: Quantitative analysis of tyrosine hydroxylase mRNA for sensitive detection of neuroblastoma cells in blood and bone marrow. Clin Chem 49:104-12, 2003). Given the heterogeneity of neuroblastoma ("NB"), studying multiple tumor markers simultaneously with special attention to tumor stem lines that circulate, was predicted to enhance both the sensitivity and the specificity of MRD measurement (Cheung I Y, Barber D, Cheung N K: Detection of microscopic neuroblastoma in marrow by histology, immunocytology, and reverse transcription-PCR of multiple molecular markers. Clin Cancer Res 4:2801-5, 1998). Historically, only markers with known expression in NB were considered. By analyzing the expression arrays of NB tumors and bone marrows, novel MRD markers were identified based on high tumor to marrow ratios. Of the 14 most promising genes identified, Cyclin D1 (CCND1) was chosen for validation in cancer patients. The clinical utility of CCND1 mRNA as a marker of metastatic cancer and its potential as an early response indicator is described herein below.

Patient Specimens and Cell Lines for Gene Expression Arrays

Tumors from 48 patients and remission marrows from 9 patients, all with stage 4 NB diagnosed after 18 months of age were used for gene expression array analysis. Patients were staged according to the International Neuroblastoma Staging System (INSS) (Brodeur, G., et al. 1993 *J Clin Oncol* 11:1466-1477). Histological sections of the tissue samples were reviewed, and the areas of interest, namely high tumor cell content and low stroma content, were manually microdissected to reduce non-tumoral tissues to achieve specimen consistency. Additionally, the following 12 NB cell lines were studied: five N-type lines: SH-SY5Y, SK-N-BE(1), SK-N-BE(2), SK-N-BE(2)M17, LAI-55N, four I-type lines (Walton, J. D., et al. 2004 *Neoplasia* 6:838-845): SK-N-LP, SK-N-ER, SK-N-JD, BE(2)C, and three S-type lines: LAI-55, SHEP1, SK-N-BE(2)S. Cells were cultured and passaged in RPMI or DME-HG with 10% FCS. Nine remission BM samples from 9 patients with stage 4 NB were also included in the study. Written informed consent was obtained from the patients and/or their guardians in accordance to the guidelines of the institutional review board of Memorial Sloan-Kettering Cancer Center (MSKCC).

Gene Expression Analysis

Total RNA was extracted using a solution of phenol and guanidine isothiocyanate, TRIZOL, (GIBCO/BRL, Gaithersburg, Md.) and purified with the Qiagen RNeasy System (Qiagen, Mississauga, ON, Canada) according to the manufacturers' recommendations. RNA concentration was determined by absorbency at 260 nm, and quality was verified by the integrity of 28S and 18S rRNA after ethidium bromide staining of total RNA samples subjected to 1.2% agarose gel electrophoresis. Total cDNA was synthesized with a T7-polyT primer and reverse transcriptase (SUPERSCRIPT II, GIBCO/BRL) before in vitro transcription with biotinylated UTP and CTP (Enzo Diagnostics, Farmingdale, N.Y.). Labeled nucleic acid target quality was assessed by Test 2 arrays and then hybridized at 45° C. for 16 hours to Affymetrix Human U95 oligonucleotide arrays (Alaminos, M., et al. 2003 Cancer Res 63(15):4538-46). After an automated process of washing and staining, absolute values of expression were calculated and normalized from the scanned array using Affymetrix Microarray Suite 5.0.

Patient Tumors of Different Histological Types

Tumor samples obtained at the time of surgery as part of the clinical diagnostic procedures were snap frozen in liquid nitrogen. These included brain tumors, breast cancers, desmoplastic small round cell tumors (DSRCT), Ewing's sarcomas, neuroblastomas, primitive neuroectodermal tumors (PNET), prostate cancers, rhabdomyosarcomas, Wilm's tumor, osteogenic sarcomas, and other soft tissue sarcomas. qRTPCR (see below) of CCND1 transcript was carried out on these samples according to the guidelines of the institutional review board of MSKCC.

Patients for Clinical Validation

Clinical validation was carried out using archived bone marrow samples from the entire cohort of 136 patients (38 with MYCN amplification of >10 MYCN copies per diploid human genome) enrolled on an immunotherapy protocol at Memorial Sloan-Kettering Cancer Center (MSKCC). This protocol utilized anti-GD2 monoclonal antibody 3F8 plus granulocyte-macrophage colony stimulating factor (GM-CSF) in children with high risk neuroblastoma following chemotherapy (Kushner, B. H., et al. 2001 *J Clin Oncol* 19:4189-4194). Treatment was administered approximately every 4-8 weeks for 4 cycles, and then periodically every 6-10 weeks for a total of 2 years as long as the patient was HAMA (human anti-mouse antibody) negative. 130 of 136 patients had metastatic stage 4, and 6 had high risk stage 3 (4 of 5 with MYCN amplification) (Brodeur, G., et al. 1993 *J Clin Oncol* 11: 1466-1477). Except for one infant with MYCN-amplified stage 4 NB, 135 of 136 were diagnosed at >12 months of age, and 126 (93%) of 136 at >18 months of age, generally regarded as the highest risk age group. Written informed consent was obtained from the patients and/or their guardians in accordance with the guidelines of the institutional review board of MSKCC. Their status of disease at protocol entry was stratified into 4 categories (Brodeur, G., et al. 1993 J Clin Oncol 11:1466-1477): CR/VGPR (complete remission/very good partial remission—complete or near-complete remission by International Neuroblastoma Response Criteria), primary refractory (resistant to induction therapy, usually with persistent marrow disease), second refractory (resistant to salvage therapy, usually with persistent marrow disease), and PD (progressive disease).

Histologic Examinations of Bone Marrow Samples

All 136 patients had marrow studies under general anesthesia prior to and after the second cycle of therapy. Each marrow examination generally consisted of six samplings from four sites: two biopsy specimens and four aspirates, as described previously (Cheung, N. K., et al. 1997 *J Clin Oncol* 15:2807-2817). After clearance of contaminating skin, bone, or endothelial cells, 2 to 2.5 mL of heparinized marrow from each aspiration site was pooled, and mononuclear cells were then isolated and cryopreserved.

Real-Time Quantitative RT-PCR

Real-time quantitative RT-PCR was performed on cryopreserved BM collected before and following treatment with 3F8/GM-CSF. Procedures for extraction of RNA from BM mononuclear cells and synthesis of cDNA were described previously (Cheung I Y, Cheung N K V: Molecular detection of GAGE expression in peripheral blood and bone marrow: utility as a tumor marker for neuroblastoma. Clin Cancer Res 3:821-826, 1997). Relative quantitation of CCND1 mRNA was achieved by using the ABI Prism 7700 Sequence Detection System (Applied Biosystems, Foster City, Calif.). Details of the procedure were reported previously (Cheung I Y, Cheung N K: Quantitation of marrow disease in neuroblastoma by real-time reverse transcription-PCR. Clin Cancer Res 7:1698-705, 200). For each unknown test sample, the amount of CCND1 transcript and its endogenous reference glyceraldehyde-3-phosphate dehydrogenase (GAPDH) was determined from the respective standard curve. These standard curves were derived from serially diluted cDNA of NB cell line NMB7. The CCND1 transcript level in units was expressed as a multiple of GAPDH expression. Samples were assayed at least twice on separate days; overall concordance was >90%, and their arithmetic means were used for outcome analyses.

Primer Sequences

The primers and probe for CCND1 were designed using the applications-based primer design software Primer Express (Applied Biosystems, ABI). The probe spanned an intron, thereby avoiding the amplification of contaminating genomic DNA present in the sample. CCND1 sense primer was 5'-CCGAGAAGCTGTGCATCTACAC-3' (SEQ ID NO: 1), antisense primer was 5'-AGGTTCCACTTGAGCTTGT-TCAC-3' (SEQ ID NO:2). CCND1 probe was FAM-5'-AG-GAGCAGCTCCATTTGCAGCAGCTC-3'-TAMRA (SEQ ID NO:3). The amplicon was 94 bp. Human endogenous control GAPDH sense primer was 5'-GAAGGTGAAG-GTCGGAGTC-3' (SEQ ID NO:4), and antisense was 5'-GAAGATGGTGATGGGATTTC-3' (SEQ ID NO:5). Probe was VIC-5'CAAGCTTCCCGTTCTCAGCC-3' (SEQ ID NO:6) (226 bp). CCND1 and GAPDH designs were based on sequence from GenBank GENBANK, accession NM_053056 and J04038, respectively. Primers and probes were synthesized by ABI.

Statistical Analysis

The upper limit of normal (ULN) for each marker was defined as mean+2SD among 40 normal marrow and blood samples. The ULN for CCND1 was 7.1, 2 for TH, and for GD2 synthase (Cheung, I. Y., et al. 2001 Clin Cancer Res 7(6):1698-705). Molecular response was defined for both CCND1 and GD2 synthase as follows: "CR (complete responder)" were patients whose pretreatment marrow samples were positive by qRT-PCR, and whose post treatment marrow samples were negative; "stable" defined patients with negative marrow samples both pre- and post-treatment; "refractory" were patients whose pre- and post-treatment marrows were both positive; "progression" defined patients with negative pretreatment samples that became positive after treatment. The normal ranges and sensitivity of GD2 synthase qRT-PCR were as previously reported (Cheung I Y, Cheung N K: Quantitation of marrow disease in neuroblastoma by real-time reverse transcription-PCR. Clin Cancer Res 7:1698-705, 200). Proportional hazards Cox models were used to determine whether CCND1 and GD2 synthase expression predicted survival. Analyses were conducted for both progression-free (PFS) and overall survival (OS). Absolute levels of pre- and post-treatment CCND1 and GD2 synthase transcripts were entered into multivariable models, and response was a categorical variable. Post-treatment MRD marker levels and MRD response were analyzed as time-dependent covariates. In these analyses, patients in "CR" were assumed to have positive MRD, whereas those in "progression" group were assumed to have negative MRD until the date of their follow-up BM.

Marker Discovery Algorithm

A total of 48 stage 4 NB tumors and 9 remission marrow samples were analyzed for entire genome-wide gene expression using the Affymetrix U-95 chip as previously described (Alaminos M, Mora J, Cheung N K, et al: Genome-wide analysis of gene expression associated with MYCN in human neuroblastoma. Cancer Res 63:4538-46, 2003). For each individual probe in the U-95 expression array, the mean expression levels among stage 4 tumors and cell lines were compared to that of remission marrows. Only genes with highly significant tumor expression were chosen (i.e. $p<8\times 10^{-7}$, using Bonferroni correction for multiple comparisons). TH, a widely accepted NB marker (Naito, H., et al. 1991 *Eur J Cancer* 27:762-765; Miyajima, Y., et al. 1995 *Cancer* 75:2757-2761; Burchill, S. A., et al. 2001 *J Clin Oncol* 19:1795-1801; Trager, C., et al. 2003 *Clin Chem* 49(1):104112; Tchirkov, A., et al. 2003 *J Hematother Stem Cell Res* 12(4):435-42), had a median tumor to mean marrow expression ratio of 37:1. Genes with ratios >37 were chosen; genes of ubiquitous nature (e.g. collagen) were excluded. 34 genes with median expression level of ≥2,500 units were identified: AF1Q, CCND1, CHGB, CNTFR, CRMP1, DDC, DPYSL3, ELAVL4, GABRB3, GAP43, GRIA2, IDAX, ISL1, K1F'1A, KIF21A, KIF5C, L1 CAM, MAB21L1, MAOA, MAP2, MEG3, NP25, NPY, PCSK1N, PFN2, PGP9.5, PHOX2B, RBP1, RGS5, RTN1, SCG2, SOX11, STMN2, TACC (see Table 1, below). A similar analysis was carried out on the 10 normal PB expression arrays obtained using the Affymetrix U95 chip A, as described at St. Jude's Children's Hospital's research website yielding the same 17 genes (out of 22 identified using BM) whose tumor to PB ratios were better that of TH (Table 1). Of these candidate genes, only PGP9.5 was previously described as a MRD marker (Mattano, L. A., et al. 1992 *Cancer Res* 52(17):4701-5). CCND1, an important gene in many human cancers, was chosen for clinical validation.

TABLE 1

Candidate MRD markers from gene expression array analyses

| Affymetrix U95 chip | Probe set | GENBANK ID | Gene Symbol | Gene Name | Tumor to BM ratio | Tumor to PB ratio |
|---|---|---|---|---|---|---|
| A | 38800_at | D45352 | STMN2 | Stathmin 2 (SCG10 protein) (Superior cervical ganglion-10 protein). | 449 | 109 |
| A | 33426_at | Y00064 | CHGB | Chromogranin B (secretogranin 1) | 287 | 38 |
| A | 39297_at | U38810 | MAB21L1 | Mab-21-like 1 (*C. elegans*) | 263 | 17 |
| A | 36149_at | D78014 | DPYSL3 | Dihydropyrimidinase-like 3 | 240 | 31 |
| A | 36990_at | X04741 | PGP9.5 | Ubiquitin carboxyl-terminal esterase L1 (ubiquitin thiolesterase) | 222 | 78 |
| A | 35778_at | AB011103 | KIF5C | Kinesin family member 5C | 203 | 46 |
| A | 37714_at | M25667 | GAP43 | Growth associated protein 43 | 182 | 49 |
| A | 40272_at | D78012 | CRMP1 | Collapsin response mediator protein 1 | 140 | 14 |
| A | 38551_at | U52112 | L1CAM | L1CAM | 110 | 27 |
| A | 36924_r_at | M25756 | SCG2 | Secretogranin II (chromogranin C) | 104 | 19 |
| A | 39990_at | U07559 | ISL1 | ISL1 transcription factor, LIM/homeodomain, (islet-1) | 93 | 25 |
| A | 35020_at | D82344 | PHOX2B | Paired mesoderm homeobox 2b | 85 | 22 |
| A | 39178_at | L10333 | RTN1 | Reticulon 1 | 71 | 51 |
| A | 38418_at | X59798 | CCND1 | Cyclin D1 (PRAD1: parathyroid adenomatosis 1) | 68 | 88 |
| A | 32650_at | Z78388 | NP25 | Neuronal protein NP22 | 66 | 11 |
| A | 41771_g_at | AA420624 | MAOA | Monoamine oxidase A | 55 | 30 |
| A | 36941_at | U16954 | AF1Q | ALL1-fused gene from chromosome 1q | 50 | 20 |
| A | 38604_at | AI198311 | NPY | Neuropeptide Y | 47 | 7 |
| A | 38634_at | M11433 | RBP1 | Retinol binding protein 1, cellular (CRBP) | 47 | 27 |
| A | 40201_at | M76180 | DDC | Dopa decarboxylase (aromatic L-amino acid decarboxylase) | 47 | 15 |
| A | 33890_at | AB008109 | RGS5 | Regulator of G-protein signalling 5 | 43 | 22 |
| A | 38839_at | AL096719 | PFN2 | Profilin 2 | 40 | 36 |
| A | 32300_s_at | M17589 | TH | Tyrosine hydroxylase | 37 | 18 |
| B | 47939_at | AA102788 | ELAVL4 | ELAV (embryonic lethal, abnormal vision, *Drosophila*)-like 4 (Hu antigen D) | 175 | — |
| B | 43976_at | AI857856 | KIF21A | Kinesin family member 21A (Kinesin-like protein KIF2) | 51 | — |
| B | 54897_at | AA167714 | MAP2 | Microtubule-associated protein 2 (MAP 2) | 44 | — |
| B | 52176_at | W21875 | KIF1A | Kinesin-like protein KIF1A (Axonal transporter of synaptic vesicles) | 41 | — |
| C | 64258_f_at | AW016235 | MEG3 | Maternally expressed 3 | 100 | — |
| C | 61320_g_at | AL037611 | TACC | T-cell activation protein | 99 | — |
| C | 63848_s_at | AI199503 | PCSK1N | Proprotein convertase subtilisin/kexin type 1 inhibitor | 81 | — |
| C | 63823_at | AL120032 | GABRB3 | Gamma-aminobutyric acid (GABA) A receptor, beta 3 | 39 | — |
| D | 73450_at | AI687064 | GRIA2 | Glutamate receptor 2 precursor (GluR-2) (GluR-B) (GluR-K2) | 59 | — |
| E | 91882_at | AI573279 | SOX11 | SRY (sex determining region Y)-box 11 | 47 | — |
| E | 73596_at | AI377558 | IDAX | Dvl-binding protein IDAX (inhibition of the Dvl and Axin complex) | 46 | — |
| E | 88926_at | AA029437 | CNTFR | Ciliary neurotrophic factor receptor | 45 | — |

Of note, many of the genes listed in Table 1, above, were not intuitively obvious as MRD markers.

Marker Validation

Marker specificity was determined by a series of normal bone marrow (BM) and normal peripheral blood (PB) (n=40), with detection threshold defined as the upper limit of normal (mean+2 SD). Marker sensitivity was established by spiking neuroblastoma cell line NMB7 at ratios ranging from 1 to 10,000 tumor cells per million normal mononuclear cells. Marker validation was based on archived BM samples from a subset of stage 4 NB patients who had undergone immunotherapy using a combination of anti-GD2 antibody 3F8 and GM-CSF (protocol 94-18) at MSKCC. Their marrow aspirates before therapy were negative by histologic examination. The post treatment samples were all before their third cycle at a median time of 1.8 months from the beginning of protocol entry. CCND1 was evaluated against the standard GD2 synthase as an early molecular response predictor. In addition, tyrosine hydroxylase (TH), which is a well-established NB marker, was also tested by qRT-PCR for comparison. The primers and probe were previously reported (Trager, C., et al. 2003 49:104-12).

Kaplan-Meier survival analyses on progression-free survival [PFS] and overall survival [OS] using the identified markers were performed. Molecular response was defined as follows: "responders" were patients whose pretreatment marrow samples were positive by qRT-PCR, and whose post treatment marrow samples were negative; "non-responders" were patients whose post treatment marrows were positive, irrespective of whether their marrows were positive or not before therapy.

Example 2

CCND1 expression in cell lines, neuroblastoma and other solid tumors CCND1 is known to be of general importance in human cancers. Activation of CDK4 and CDK6 by CCND1 induces phosphorylation of the retinoblastoma protein Rb, then the release of E2F transcription factors and subsequent progression of the cell cycle from G1 to S. Moreover, CCND1 is known for its overexpression in a wide variety of malignant adult (Donnellan, R., et al. 1998 *Mol Pathol* 51:1-7; Bali, A., et al. 2004 *Clin Cancer Res* 10:5168-77) and pediatric cancers (Baer, C., et al. 2004 *Int J Cancer* 110:687-94). In rhabdomyosarcoma and Ewing's sarcoma, expression array analysis has also identified CCND1 as a highly expressed tumor transcript (Baer, C., et al. 2004 *Int J Cancer* 110:687-94). Besides its clinical importance among embryonal tumors and sarcomas,

*Pathol* 51:1-7). It is overexpressed in nearly half of all breast cancers and in virtually all lobular carcinomas and estrogen-receptor positive ductal carcinomas. In endometrial adenocarcinoma, its expression was correlated with histological grade and proliferative activity (Nishimura, Y., et al. 2004 *Anticancer Res* 24:2185-91), while in small adenocarcinoma of lung (Oshita, F., et al. 2004 *Am J Clin Oncol* 27:425-8) and ovarian cancer (Barbieri, F., et al. 2004 *Oncology* 66:310-5), it was predictive of poor survival. In prostate cancer, it was thought to be important for tumorigenicity (Gao, H., et al. 2004 *Proc Natl Acad Sci USA* 101:17204-17209) and androgen-independence (Sirotnak, F. M., et al. 2004 *Mol Carcinog* 41:150-63).

As mentioned above, sensitivity of CCND1 mRNA by qRT-PCR was established by spiking NMB7 cells at ratios ranging from 1 to 10,000 tumor cells per $10^6$ normal mononuclear cells. The level of CCND1 transcript for a tumor content of $1/10^6$ was 9.7 units. CCND1 expression was detected in 10 NB cell lines, irrespective of subtype (N, S and I lines, median 315) (Table 2, below). Among a panel of 133 human solid tumors, CCND1 expression in breast cancer (median 2218) and Ewing's sarcoma/PNET (median 1987) were comparable to that of 39 NB tumors of all clinical stages (median 2157).

TABLE 2

CCND1 expression (in transcript units) among human solid tumors and NB cell lines

| Tumor type | Sample size | Median | 25th Centile | 75th Centile |
|---|---|---|---|---|
| NB-cell lines* | 10 | 315 | 234 | 371 |
| NB-STAGE1 | 4 | 4590 | 3533 | 5318 |
| NB-STAGE2 | 5 | 1069 | 1037 | 3073 |
| NB-STAGE3 | 5 | 1749 | 1694 | 2034 |
| NB-STAGE4 | 20 | 2050 | 851 | 3030 |
| NB-STAGE4S | 5 | 2244 | 2188 | 5413 |
| EW/PNET | 12 | 1987 | 1125 | 3695 |
| Breast CA | 22 | 2218 | 1031 | 3453 |
| DSRCT | 7 | 856 | 747 | 1141 |
| Prostate CA | 12 | 719 | 509 | 962 |
| Soft tissue sarcomas | 12 | 371 | 247 | 738 |
| Brain tumors | 12 | 137 | 44 | 244 |
| RMS | 7 | 106 | 39 | 514 |
| Wilm's tumor | 5 | 68 | 17 | 99 |
| OS | 5 | 8 | 7 | 76 |

Example 3

Molecular Response by CCND1 and Prognostic Significance

QRT-PCR of CCND1 mRNA and Correlation with TH and GD2 Synthase mRNA

Of the entire cohort of 136 patients, 124 patients had follow-up BM samples after treatment cycle #2, at a median of 2.5 months from protocol entry; 84% (104/124) were collected prior to treatment cycle #3, and 98% (122/124) collected prior to cycle #4. Median transcript levels of CCND1, and two established NB markers TH and GD2 synthase stratified according to disease status at protocol entry, are detailed in Table 3, below.

TABLE 3

Median transcript levels (units) of molecular markers CCND1, GD2 synthase, and tyrosine hydroxylase stratified according to patient status at protocol entry

| Tumor Marker | | Number of patients | Number of patients positive for marker (Median) | | | | |
|---|---|---|---|---|---|---|---|
| | | | Overall | CR/VGPR* | 1° Refractory | 2° Refractory | PD |
| CCND1 | Pretreatment | 136 | 67 | 32 | 17 | 7 | 11 |
| | | | (15.7) | (15.5) | (11.9) | (10.9) | (52.0) |
| | Post-treatment | 124 | 61 | 19 | 24 | 9 | 9 |
| | | | (18.8) | (13.6) | (12.0) | (101.9) | (303.3) |
| GD2 synthase | Pretreatment | 136 | 54 | 21 | 17 | 6 | 10 |
| | | | (12.7) | (11.8) | (11.7) | (13.1) | (49.3) |
| | Post-treatment | 124 | 36 | 10 | 11 | 7 | 8 |
| | | | (41) | (17.8) | (19.9) | (355.3) | (395.7) |
| Tyrosine hydroxylase | Pretreatment | 136 | 37 | 6 | 17 | 6 | 8 |
| | | | (16.2) | (12.8) | (12.4) | (17.8) | (212.8) |
| | Post-treatment | 124 | 31 | 4 | 12 | 8 | 7 |
| | | | (50.5) | (63.5) | (18.0) | (84.9) | (205.0) |

*CR/VGPR: complete remission/very good partial remission, 1° refractory: primary refractory, 2° refractory: secondary refractory, PD: progressive disease.

Figure 1B:
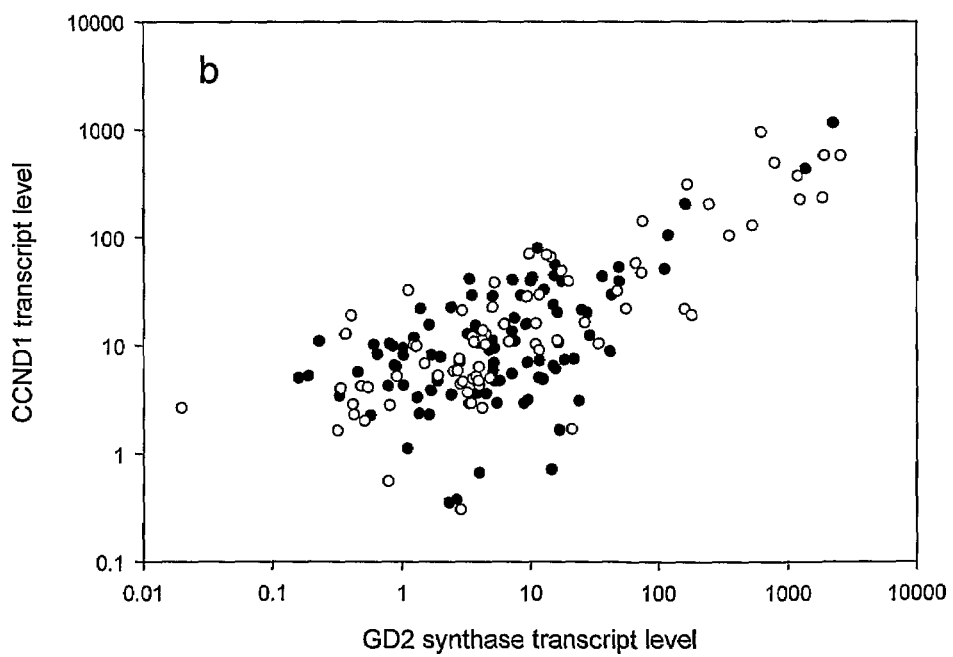

GD2 synthase transcript was previously shown to correlate with the number of tumor cells in BM (Cheung, I. Y., et al. 2001 *Clin Cancer Res* 7(6):1698-705). Correlation coefficient between the transcript level of CCND1 and TH, as well as between CCND1 and GD2 synthase was 0.91 and 0.97, respectively for the pretreatment marrows. It was 0.30 and 0.75, respectively for the post-treatment samples (FIG. 1).

Prognostic Significance of Early Molecular Response

Among these 124 patients, there were 81 progression events (65%) and 62 deaths (50%). Median follow-up for survivors was 37 months for PFS and 34 months for OS. For CCND1 molecular response, there were 25 "CR", 38 "stable", 33 "refractory" and 28 "progression". Univariate predictors of OS using CCND1, TH and GD2 synthase are detailed in Table 4, below.

TABLE 4

Univariate analysis of overall survival using molecular markers CCND1, TH and GD2 synthase

| | Overall Survival | | |
| --- | --- | --- | --- |
| Variable | Hazard ratio | 95% C.I. | p |
| CCND1 pre-treatment* | 1.67 | 1.01, 2.77 | 0.048 |
| CCND1 post-treatment* | 1.33 | 1.17, 1.51 | <0.0005 |
| CCND1 response type | | | |
| CR | Reference | | |
| Stable | 2.71 | 1.01, 7.31 | 0.049 |
| Refractory | 4.07 | 1.51, 10.98 | 0.006 |
| Progression | 5.51 | 2.06, 14.72 | 0.001 |
| TH pre-treatment* | 1.54 | 1.2, 1.97 | 0.001 |
| TH post-treatment* | 1.16 | 1.04, 1.29 | 0.006 |

TABLE 4-continued

Univariate analysis of overall survival using molecular markers CCND1, TH and GD2 synthase

| | Overall Survival | | |
| --- | --- | --- | --- |
| Variable | Hazard ratio | 95% C.I. | p |
| TH response type | | | |
| CR | Reference | | |
| Stable | 0.94 | 0.44, 2.01 | 0.9 |
| Refractory | 3.41 | 1.38, 8.43 | 0.008 |
| Progression | 3.54 | 1.55, 8.07 | 0.003 |
| GD2 synthase pre-treatment* | 1.19 | 1.03, 1.37 | 0.015 |
| GD2 synthase posttreatment* | 1.14 | 1.08, 1.19 | <0.0005 |
| GD2 synthase response type | | | |
| CR | Reference | | |
| Stable | 1.58 | 0.74, 3.38 | 0.2 |
| Refractory | 3.66 | 1.6, 8.4 | 0.002 |
| Progression | 5.04 | 2.1, 12.07 | <0.0005 |

*Hazard ratio calculated for each 100 transcript units.

Figure 2:
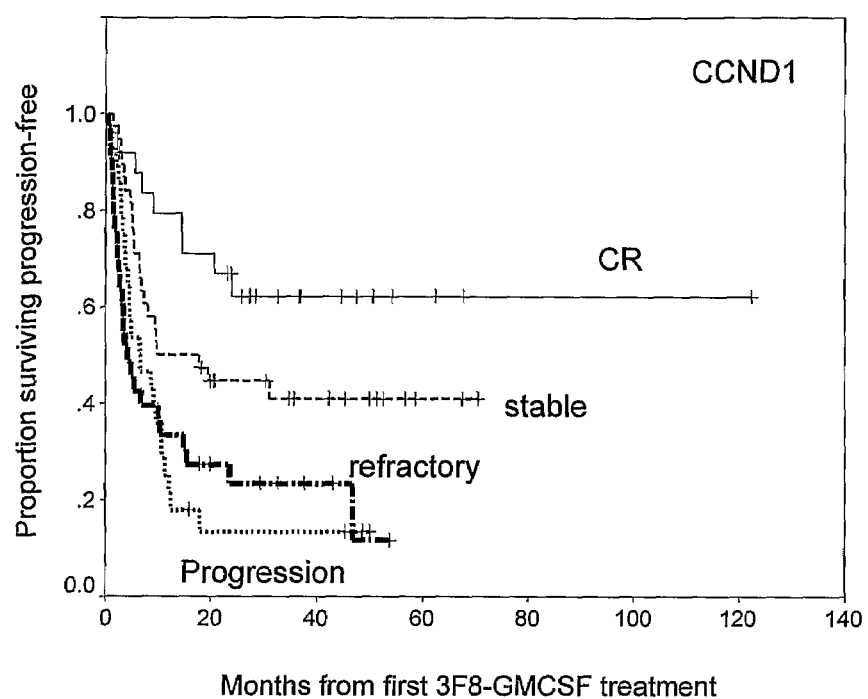
FIG. 2 shows a Kaplan Meier plot of progression-free survival with respect to CCND1 early molecular response among 124 high risk neuroblastoma patients treated with an immunotherapy protocol using anti-GD2 antibody 3F8 plus GM-CSF. Follow-up marrows were evaluated at 2.5 months from protocol entry.
Figure 3:
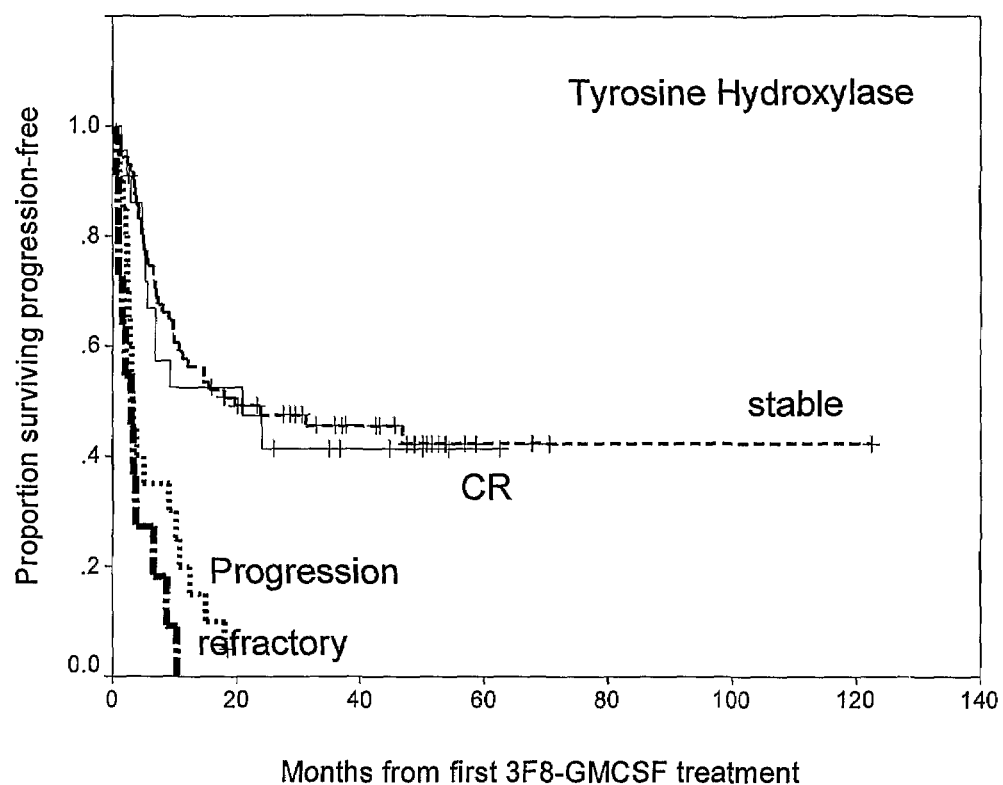
FIG. 3 shows a Kaplan Meier plot of progression-free survival with respect to tyrosine hydroxylase early molecular response among 124 patients treated with 3F8+GM-CSF.
Figure 4:
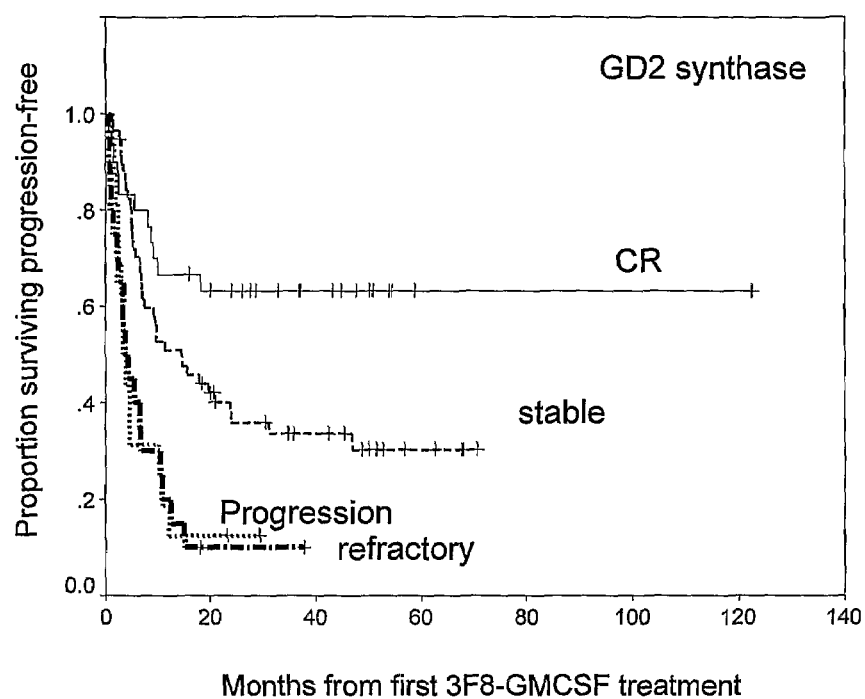
FIG. 4 shows a Kaplan Meier plot of progression-free survival with respect to GD2 synthase early molecular response among 124 patients treated with 3F8+GM-CSF.

Both pre- and post-treatment MRD levels were statistically significant; molecular response status of "refractory" or "progression" influenced outcome adversely, the latter category being the worst for all three markers. Early CCND1 marrow response was highly predictive of PFS (p=0.001, FIG. 2) and OS (p=0.001). Similar outcomes were found when NB markers TH and GD2 synthase were tested (FIGS. 3 and 4, respectively).

Since pretreatment levels were weak univariate predictors, they were omitted from the multivariable models. Both molecular response and absolute post-treatment levels of CCND1, TH, and GD2 synthase were strongly associated with PFS and OS (Table 5, below).

TABLE 5

Multivariable outcome analysis of molecular markers CCND1, TH and GD2 synthase

| | Overall Survival | | | Progression-free Survival | | |
| --- | --- | --- | --- | --- | --- | --- |
| | Hazard ratio | 95% C.I. | p | Hazard ratio | 95% C.I. | p |
| CCND1 Response type | | | | | | |
| CR | Reference | | | Reference | | |
| Stable | 2.73 | 1.01, 7.35 | 0.047 | 1.69 | 0.8, 3.57 | 0.17 |
| Refractory | 3.28 | 1.19, 9.06 | 0.022 | 2.31 | 1.07, 4.95 | 0.032 |
| Progression | 4.8 | 1.79, 12.92 | 0.002 | 3.14 | 1.48, 6.63 | 0.003 |
| Posttreatment level* | 1.27 | 1.1, 1.47 | 0.001 | 1.54 | 1.31, 1.81 | p < 0.0005 |
| TH Response type | | | | | | |
| CR | Reference | | | Reference | | |
| Stable | 0.94 | 0.44, 2.01 | 0.9 | 0.91 | 0.48, 1.74 | 0.8 |
| Refractory | 2.77 | 1.08, 7.08 | 0.033 | 5.05 | 2.12, 12.04 | p < 0.0005 |
| Progression | 2.86 | 1.23, 6.64 | 0.015 | 3.07 | 1.47, 6.43 | 0.003 |
| Posttreatment level* | 1.08 | 1.02, 1.15 | 0.013 | 1.05 | 1, 1.09 | 0.027 |
| GD2 synthase Response type | | | | | | |
| CR | Reference | | | Reference | | |
| Stable | 1.58 | 0.74, 3.38 | 0.2 | 2.09 | 1.07, 4.09 | 0.032 |
| Refractory | 3.05 | 1.3, 7.17 | 0.01 | 4.55 | 2.08, 9.96 | p < 0.0005 |
| Progression | 3.61 | 1.44, 9.08 | 0.006 | 4.31 | 1.9, 9.78 | p < 0.0005 |
| Posttreatment level* | 1.09 | 1.03, 1.16 | 0.003 | 1.08 | 1.03, 1.14 | 0.002 |

Hazard ratio calculated for each 100 transcript units.

The concordance indices for the multivariable models for TH, CCND1, and GD2 synthase were 0.636, 0.662 and 0.667, respectively. The analysis was subsequently restricted to 92 patients who had been followed for at least two years and who did not relapse prior to the date of follow-up marrow. Of 15 patients who were TH-positive in their post-treatment marrows, all 15 relapsed. However, 41/77 TH-negative patients also progressed; 26 of these 77 patients were CCND1-positive, of whom 16 progressed. Assuming the misclassification cost of a false positive was ≤1.5 times than that of a false negative, addition of CCND1 to TH for MRD surveillance should be informative.

Prognostic Importance of CCND1 Early Response in Patients with MRD

Among the 74 stage 4 patients with MRD (i.e., histologically negative marrows) at protocol entry, 66 had follow up marrow studies; 79% (52/66) of them were in CR/VGPR prior to treatment. When molecular responses were analyzed (Table 6, below), only patients with CR/VGPR (66%) or primary refractory disease (33%) before treatment achieved either "CR" or "stable" molecular response.

TABLE 6

CCND1 molecular responses (percent) in 66 stage 4 patients with minimal residual disease before treatment

| Clinical status before treatment | Molecular response* | | | |
|---|---|---|---|---|
| | CR | Stable | Refractory | Progression |
| CR/VGPR | 14/52 (27) | 20/52 (39) | 12/52 (23) | 6/52 (13) |
| Primary refractory | 1/9 (11) | 2/9 (22) | 3/9 (33) | 3/9 (33) |
| Secondary refractory | 0/3 (0) | 0/3 (0) | 3/3 (100) | 0/3 (0) |
| Progressive disease | 0/2 (0) | 0/2 (0) | 2/2 (100) | 0/2 (0) |

Figure 5:
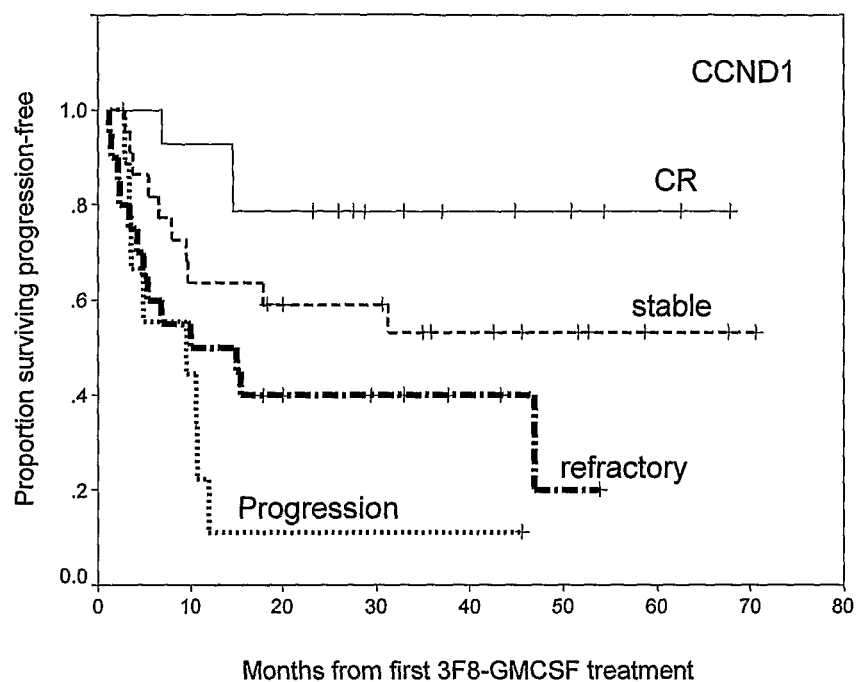
FIG. 5 shows a Kaplan Meier plot of progression-free survival with respect to CCND1 early molecular response among 66 stage 4 neuroblastoma patients with minimum residual disease before treatment.

CCND1 (p=0.011, FIG. 5), TH (p=0.039) and GD2 synthase (p=0.005) were all predictive of PFS for these MRD patients. Multivariable analyses could not be done, since there were only 15 deaths in this subgroup, too few for reliable evaluation of models with four variables.

Marker discovery can be more efficient when the context (namely, BM or PB) in which the molecular information will be most useful is being considered. Focus is placed herein on genes differentially expressed in tumors over normal BM or PB. In addition, a genome-wide annotated gene expression approach was used, such that potential marker candidates can be directly compared and ranked, so as to reduce false leads. This marker discovery and validation approach has particular relevance for orphan diseases such as neuroblastoma, where the repertoire of known tumor markers is small. Although the Affymetrix U-95A-E chips were employed herein, the described strategy should be applicable to other genome-wide expression platforms.

The fact that CCND1 shows promise as a potential early response marker is particularly relevant for metastatic NB, where alternative treatment options must be timely (Cheung, I. Y., et al. 2003 J Clin Oncol 21(20):3853-8). Since CCND1 expression is also high in breast cancer and Ewing's sarcoma/PNET, it may have clinical utility for these tumors. The general approach of marker discovery by identifying genes differentially expressed in tumors over normal BM or PB, and validation using archived BM or PB deserve further investigations.

Example 4

Identification of Markers for Melanoma

The process of identification of MRD markers described above for neuroblastoma was applied to melanoma, with the following filters/parameters applied:

Affymetrix U95A: 20 cell lines, 9 tumors, 9 remission BM, and 19 normal PB samples;

Genes with tumor to bone marrow gene expression signal ratio>30, or tumor to peripheral blood gene expression signal ratio>20;

ttest $p<4 \times 10^{-6}$, better than tyrosinase ($p=3 \times 10^{-5}$), a widely used melanoma marker;

The following genes are excluded: of ubiquitous nature (e.g. collagen), with pseudogenes, BM expression by electronic northern or SAGE, and median expression level<1,000 units.

MRD Markers thus Identified for Melanoma:
MYO10 (myosin X);
TFAP2A (transcription factor AP-2 alpha, activating enhancer-binding protein 2 alpha);
ERBB3 (v-erb-b2 avian erythroblastic leukemia viral oncogene homolog 3);
PLP1 (Pelizaeus-Merzbacher disease, spastic paraplegia 2, uncomplicated) proteolipid protein 1; and CCND1.

Example 5

Identification of Markers for Osteosarcoma

The process of identification of MRD markers described above for neuroblastoma was applied to osteosarcoma, with the following filters/parameters applied:

Affymetrix U95: 30 tumors (15 high grade), 9 remission BM, 19 normal PB samples;

Genes with tumor to PB gene expression signal ratio>20;

ttest $p<8 \times 10^{-7}$ for all tumor to BM and tumor to PB gene expression signal ratios;

The following genes are excluded: of ubiquitous nature (e.g. collagen), with pseudogenes, BM expression by electronic northern or SAGE, and median expression level<1,000 units.

MRD markers thus identified for osteosarcoma are listed in Table 7, below:

TABLE 7

| Gene Sym | median all tumor | median grIII | All tumor | | All tumor | | GrIII | | GrIII | | mean | |
|---|---|---|---|---|---|---|---|---|---|---|---|---|
| | | | to BM | ttest:BM | to PB | ttest:PB | to BM | ttest | to PB | ttest | BM | PB |
| FAP | 2538 | 4280 | 247 | 1.E−07 | 31 | 2.E−07 | 416 | 2.E−05 | 53 | 3.E−05 | 10 | 81 |
| OSF-2 | 3553 | 3458 | 117 | 3.E−09 | 22 | 6.E−09 | 114 | 1.E−05 | 22 | 2.E−05 | 30 | 159 |
| THBS2 | 4635 | 5139 | 102 | 7.E−10 | 21 | 2.E−09 | 113 | 2.E−05 | 24 | 4.E−05 | 46 | 216 |
| MYO1B | 2505 | 2798 | 48 | 1.E−11 | 10 | 5.E−11 | 54 | 4.E−07 | 11 | 9.E−07 | 52 | 261 |
| LUM | 4027 | 4353 | 48 | 4.E−11 | 24 | 6.E−11 | 52 | 5.E−06 | 26 | 6.E−06 | 83 | 165 |

TABLE 7-continued

| Gene Sym | median all tumor | median grIII | All tumor to BM | All tumor ttest:BM | All tumor to PB | All tumor ttest:PB | GrIII to BM | GrIII ttest | GrIII to PB | GrIII ttest | mean BM | mean PB |
|---|---|---|---|---|---|---|---|---|---|---|---|---|
| FAT | 2885 | 3077 | 40 | 6.E−11 | 9 | 3.E−10 | 42 | 8.E−07 | 10 | 2.E−06 | 73 | 316 |
| LOX | 3417 | 3903 | 34 | 6.E−11 | 13 | 2.E−10 | 39 | 7.E−06 | 15 | 1.E−05 | 100 | 264 |
| CCND1 | 5487 | 5458 | 21 | 3.E−09 | 27 | 2.E−09 | 21 | 1.E−05 | 27 | 1.E−05 | 260 | 200 |
| THBS2 | 1866 | 2578 | 118 | 1.E−07 | 19 | 3.E−07 | 162 | 1.E−04 | 26 | 2.E−04 | 16 | 99 |
| IGSF4 | 1992 | 1891 | 62 | 5.E−07 | 19 | 8.E−07 | 59 | 6.E−05 | 18 | 9.E−05 | 32 | 107 |
| LOC92689 | 1051 | 1115 | 30 | 8.E−10 | 10 | 3.E−09 | 32 | 5.E−05 | 11 | 8.E−05 | 35 | 102 |
| SEPT10 | 1074 | 1257 | 30 | 3.E−09 | 7 | 2.E−08 | 35 | 8.E−05 | 8 | 2.E−04 | 36 | 158 |
| ME1 | 1489 | 1375 | 24 | 1.E−08 | 12 | 2.E−08 | 22 | 7.E−05 | 11 | 1.E−04 | 63 | 126 |

Example 6

Identification of Markers for Breast Cancer

Even though metastatic breast cancer cells circulate in blood, rare circulating tumor cells (CTC) are difficult to detect. To date, few accurate diagnostic tests are available (Gilbey, A. M., et al. 2004 *J Clin Pathol* 57:903-11; Cristofanilli, M., et al. 2004 *N Engl J Med* 351:781-91). The latest advances in quantitative polymerase chain reaction (PCR) and reverse transcription (RT)-PCR offer exceptional sensitivity in detecting DNA and RNA, respectively. Their successful clinical translation is particularly evident in HIV, hepatitis, and EBV infections where the target has an exquisitely specific signature. However, tumor-specific markers or genetic aberrations do not exist in the majority of breast cancer. Since standard serum markers lack sensitivity and specificity (e.g. CA 15.3 (MUC1), CEA and cytokeratins), numerous potential molecular markers have been explored. These include telomerase, cytokeratins (CK19, CK20, CK8, CK16), mammaglobin B, CEA, maspin, MUC1, PIP, HER-2, EGFR, stromylsin-3, PTHrP, and GA733.2. Unfortunately, their clinical utility has uniformly been suboptimal (Jiang, W. G., et al. 2002 *Crit Rev Oncol Hematol* 43:13-31). A detailed analysis showed that previous efforts in MRD marker discovery have focused primarily on known breast cancer genes, typically neglecting the critical blood compartment in which they are measured. There is also the tendency to overlook the inherent heterogeneity of breast cancer. It is likely that a panel of markers will be necessary for the detection of every CTC.

The process of identification of MRD markers described above for neuroblastoma was applied to breast cancer, with the following filters/parameters applied:

Affymetrix U133: 125 tumors (12 metastatic), 10 cell lines, 10 normal PB samples.

Genes with tumor to PB gene expression signal ratio>20, or cell line to PB gene expression signal ratio>9 ttest<$4\times10^{-7}$ for all tumor to BM and all tumor to PB

The following genes are excluded: of ubiquitous nature (e.g. collagen), with pseudogenes, BM expression by electronic northern or SAGE, and median expression level<1000 units.

MRD markers thus identified for breast cancer are listed in Table 8, below:

TABLE 8

| Gene Symbol | median all tumor | median mets | median cellline | mean PB | All tumor to PB | All tumor ttest | mets to PB | mets ttest | cell line to PB | cell line ttest |
|---|---|---|---|---|---|---|---|---|---|---|
| MGP | 11508 | 9165 | 3228 | 54 | 212 | 3.E−32 | 169 | 3.E−04 | 59 | 3.E−02 |
| FXYD3 | 3154 | 4272 | 4455 | 32 | 100 | 8.E−28 | 135 | 7.E−04 | 141 | 5.E−04 |
| IGFBP5 | 4553 | 2937 | 6783 | 46 | 98 | 2.E−20 | 63 | 4.E−02 | 146 | 6.E−03 |
| CDH1 | 3903 | 5431 | 7713 | 47 | 84 | 2.E−35 | 116 | 8.E−05 | 165 | 6.E−04 |
| TACSTD2 | 5567 | 5804 | 4841 | 96 | 58 | 3.E−37 | 61 | 3.E−04 | 51 | 3.E−04 |
| TACSTD1 | 2764 | 3980 | 3627 | 68 | 40 | 5.E−45 | 58 | 6.E−06 | 53 | 9.E−06 |
| AGR2 | 3636 | 7727 | 7987 | 90 | 40 | 8.E−19 | 86 | 1.E−03 | 89 | 7.E−04 |
| PBX1 | 2023 | 2457 | 3597 | 55 | 37 | 2.E−36 | 45 | 8.E−05 | 66 | 1.E−05 |
| CRABP2 | 2905 | 4321 | 2090 | 130 | 22 | 1.E−20 | 33 | 2.E−03 | 16 | 1.E−02 |
| KRT7 | 1892 | 2697 | 783 | 26 | 72 | 2.E−25 | 103 | 1.E−02 | 30 | 3.E−02 |
| SCNN1A | 1467 | 1543 | 1176 | 40 | 37 | 9.E−26 | 39 | 5.E−04 | 30 | 9.E−03 |
| CLDN3 | 1020 | 2024 | 1422 | 31 | 33 | 4.E−22 | 65 | 2.E−04 | 46 | 2.E−03 |
| RAI3 | 1258 | 1316 | 484 | 40 | 32 | 1.E−18 | 33 | 2.E−03 | 12 | 1.E−02 |
| MYO6 | 1044 | 1809 | 749 | 43 | 25 | 2.E−36 | 43 | 2.E−05 | 18 | 6.E−06 |
| CCND1 | 1171 | 1209 | 1630 | 48 | 24 | 3.E−14 | 25 | 2.E−02 | 34 | 4.E−04 |

Example 7

Identification of Markers for Small Cell Lung Cancer (SCLC)

Even though metastatic SCLC cells circulate in blood, rare circulating tumor cells (CTC) are difficult to detect. To date, few accurate diagnostic tests are available. The latest advances in quantitative polymerase chain reaction (PCR) and reverse transcription (RT)-PCR offer exceptional sensitivity in detecting DNA and RNA, respectively. Their successful clinical translation is particularly evident in HIV, hepatitis, and EBV infections where the target has an exquisitely specific signature. However, tumor-specific markers or genetic aberrations do not exist in the majority of SCLC. Most standard serum markers lack sensitivity and specificity, and few if any molecular markers have been explored. A detailed analysis showed that previous efforts in MRD marker discovery have focused primarily on known SCLC genes, typically neglecting the critical blood compartment in which they are measured.

The process of identification of MRD markers described above for neuroblastoma was applied to small cell lung cancer, with the following filters/parameters applied:

Affymetrix U95: 6 tumors, 9 remission BM, 19 normal PB samples;

Genes with tumor to PB gene expression signal ratio>37;

The following genes are excluded: of ubiquitous nature (e.g. collagen), with pseudogenes, BM expression by electronic northern or SAGE, and median expression level<1000 units.

MRD markers thus identified for small cell lung cancer are listed in Table 9, below:

TABLE 9

| Gene Symbol | tumor to BM | tumor to PB | median tumor | mean PB | mean BM |
|---|---|---|---|---|---|
| ASCL1 | 468 | 299 | 26307 | 88 | 56 |
| SCNN1A | 96 | 39 | 3635 | 93 | 38 |
| GRP | 85 | 49 | 4527 | 92 | 53 |
| ISL1 | 76 | 20 | 5381 | 264 | 70 |
| NP25 | 60 | 10 | 2762 | 289 | 46 |
| CHGA | 57 | 8 | 1532 | 196 | 27 |
| INSM1 | 54 | 13 | 2464 | 197 | 45 |
| SCG2 | 47 | 9 | 1270 | 149 | 27 |
| DDC | 44 | 14 | 2762 | 196 | 62 |
| IGSF4 | 42 | 12 | 1330 | 107 | 32 |
| CRMP1 | 37 | 4 | 1240 | 347 | 33 |
| OSF-2 | 37 | 7 | 1110 | 159 | 30 |

Example 8

Identification of Markers for Squamous Cell Lung Cancer (SCC)

The process of identification of MRD markers described above for neuroblastoma was applied to squamous cell lung cancer with the following filters/parameters applied:

Affymetrix U95: 21 tumors, 9 remission bone marrow, 19 normal peripheral blood samples;

Genes with tumor to bone marrow gene expression signal ratio>37;

ttest p<4×10$^{-6}$;

The following genes are excluded: of ubiquitous nature (e.g. collagen), with pseudogenes, BM expression by electronic northern or SAGE, and median expression level<500 units.

MRD markers thus identified for squamous cell lung cancer are listed in Table 10, below:

TABLE 10

| Gene Symbol | tumor to BM | tumor ttest | tumor to PB | ttest | median tumor | mean PB | mean BM |
|---|---|---|---|---|---|---|---|
| OSF-2 | 76 | 4.E-08 | 14 | 9.E-08 | 2294 | 159 | 30 |
| TFAP2A | 74 | 2.E-07 | 9 | 7.E-07 | 1933 | 208 | 26 |
| SOX2 | 69 | 8.E-06 | 16 | 1.E-05 | 1129 | 70 | 16 |
| S100A2 | 52 | 6.E-06 | 36 | 7.E-06 | 10552 | 292 | 201 |

Example 9

Identification of Markers for Prostate Cancer

Prostate cancer patients are often told that they have "no evidence of disease" after initial therapy. Yet it is crucial for these "cured" patients to have careful follow-up and monitoring for recurrence. Unfortunately, by the time such recurrence is detected by scan or symptoms, it is often too late for curative intervention. Prostate-specific antigen (PSA) is routinely used in the care of patients with prostate cancer. An important concept in prostate cancer management is that of "biochemical relapse", where patients are considered to have disease recurrence on the basis of a rising PSA even in the absence of clinical, radiological or histological evidence of disease (Khan, M. A., et al. 2004 Curr Urol Rep 5: 179-87). Targeting subclinical prostate cancer is a logical alternative to the traditional approach of waiting for signs or symptoms of gross disease. Instead of the "killing paradigm", the alternative strategy of "regulatory control" is highly relevant in today's cancer management (Schipper, H., et al. 1995 J Clin Oncol 13:801-7). New classes of agents such as angiogenesis inhibitors, growth modulators or vaccines may not result in rapid tumor shrinkage. For these agents, since the maximum tolerated dose may not be the optimal biologic dose, the typical Phase I endpoint of toxicity is also inappropriate. Yet, detecting MRD has been a continuing challenge. Except for PSA, PSMA and hK-2, few markers are available for clinical validation. Given the inherent heterogeneity of prostate, a single marker is unlikely to be enough for detecting all CTC.

The process of identification of MRD markers described above for neuroblastoma was applied to prostate cancer, with the following filters/parameters applied:

Affymetrix U133: 86 tumors (8 metastatic), 10 normal PB samples;

Genes with tumor to PB gene expression signal ratio>20, cell line to PB gene expression signal ratio>9;

ttest p<4×10$^{-7}$ for all tumor to PB ratio>50;

The following genes are excluded: of ubiquitous nature (e.g. collagen), with pseudogenes, BM expression by electronic northern or SAGE, median expression (all tumors) <2000, and median expression level (metastatic tumors) <1000.

MRD markers thus identified for prostate cancer are listed in Table 11, below:

TABLE 11

| Gene Symbol | median mets | median all tumor | median PB | all tumor to PB | all tumor ttest | mets to PB | mets ttest |
|---|---|---|---|---|---|---|---|
| FXYD3 | 1714 | 6042 | 32 | 191 | 7.E-30 | 54 | 1.E-01 |
| MGP | 2333 | 7866 | 54 | 145 | 3.E-33 | 43 | 2.E-03 |
| ALDH1A3 | 2197 | 8477 | 62 | 136 | 2.E-36 | 35 | 6.E-03 |
| CDH1 | 4718 | 6258 | 47 | 134 | 6.E-49 | 101 | 6.E-03 |
| TACSTD2 | 5836 | 10855 | 96 | 114 | 2.E-49 | 61 | 9.E-04 |
| HOXB13 | 2100 | 2157 | 20 | 107 | 5.E-33 | 104 | 4.E-03 |
| IGFBP5 | 4909 | 4197 | 46 | 91 | 3.E-33 | 106 | 3.E-03 |
| TSPAN-1 | 3730 | 7613 | 97 | 79 | 2.E-28 | 39 | 7.E-03 |
| AGR2 | 2622 | 6424 | 90 | 71 | 4.E-25 | 29 | 5.E-02 |
| PSMAL/GCP III | 2130 | 2546 | 44 | 58 | 2.E-18 | 49 | 3.E-02 |
| FOLH1 | 6830 | 6712 | 124 | 54 | 8.E-23 | 55 | 2.E-02 |
| TACSTD1 | 4657 | 3471 | 68 | 51 | 5.E-36 | 68 | 1.E-03 |

Example 10

Identification of Markers for Ewing's Sarcoma

The process of identification of MRD markers described above for neuroblastoma was applied to Ewing's sarcoma, with the following filters/parameters applied:

Affymetrix U133: 10 cell lines, 28 tumors; 10 normal PB samples;

Genes with tumor to PB gene expression signal ratio>20; ttest p<5×10$^{-7}$;

The following genes are excluded: of ubiquitous nature (e.g. collagen), with pseudogenes, BM expression by electronic northern or SAGE, and median expression level<1,000 units.

MRD markers thus identified for Ewing's sarcoma are listed in Table 12, below:

TABLE 12

| | median mets | liver mets | lung mets | median primary | mean PB | mets to PB | mets ttest | liver mets to PB | lung mets to PB | primary to PB | primary ttest |
|---|---|---|---|---|---|---|---|---|---|---|---|
| FABP1 | 4436 | 6245 | 3252 | 3081 | 13 | 348 | 2.E−08 | 491 | 255 | 242 | 1.E−08 |
| FXYD3 | 4858 | 5401 | 3899 | 4897 | 32 | 154 | 3.E−11 | 171 | 123 | 155 | 1.E−16 |
| TACSTD1 | 10370 | 10722 | 10293 | 8020 | 68 | 152 | 1.E−24 | 157 | 151 | 117 | 1.E−34 |
| CDH1 | 5987 | 6203 | 5978 | 5741 | 47 | 128 | 1.E−19 | 133 | 128 | 123 | 9.E−31 |
| CEACAM5 | 25918 | 24386 | 26392 | 18860 | 323 | 80 | 3.E−22 | 76 | 82 | 58 | 2.E−23 |
| kindlin 1 | 3636 | 4881 | 2643 | 2844 | 50 | 73 | 5.E−11 | 98 | 53 | 57 | 3.E−17 |
| LUM | 2042 | 1565 | 3960 | 2965 | 36 | 57 | 6.E−11 | 44 | 111 | 83 | 3.E−17 |
| KRT20 | 3062 | 3603 | 2883 | 3308 | 60 | 51 | 2.E−11 | 60 | 48 | 55 | 9.E−14 |
| AGR2 | 4464 | 5565 | 3955 | 6959 | 90 | 49 | 4.E−14 | 62 | 44 | 77 | 1.E−16 |
| RAI3 | 2693 | 3421 | 2288 | 2729 | 55 | 49 | 5.E−12 | 63 | 42 | 50 | 1.E−15 |
| MGP | 2440 | 1365 | 3849 | 1173 | 54 | 45 | 4.E−10 | 25 | 71 | 22 | 5.E−06 |
| LGALS4 | 7705 | 7894 | 7274 | 8978 | 182 | 42 | 2.E−18 | 43 | 40 | 49 | 5.E−25 |
| CLDN3 | 1985 | 2097 | 1974 | 2230 | 31 | 64 | 2.E−13 | 68 | 64 | 72 | 1.E−19 |
| MET | 1695 | 1769 | 1432 | 1587 | 27 | 63 | 3.E−17 | 66 | 53 | 59 | 2.E−22 |
| SCNN1A | 1965 | 2150 | 1594 | 2526 | 40 | 50 | 2.E−10 | 54 | 40 | 64 | 3.E−15 |
| TM4SF6 | 1816 | 1996 | 1746 | 1802 | 43 | 43 | 4.E−17 | 47 | 41 | 42 | 4.E−18 |
| THBS1 | 1005 | 979 | 1018 | 823 | 25 | 41 | 6.E−16 | 40 | 41 | 33 | 1.E−15 |
| CCL20 | 1068 | 1091 | 1051 | 1645 | 27 | 39 | 3.E−07 | 40 | 39 | 61 | 3.E−08 |
| IGFBP5 | 1787 | 776 | 3413 | 2610 | 46 | 39 | 3.E−08 | 17 | 74 | 56 | 2.E−10 |
| PLOD2 | 1638 | 1638 | 1605 | 1175 | 45 | 36 | 8.E−15 | 36 | 36 | 26 | 2.E−19 |
| PHLDA2 | 1029 | 1417 | 897 | 1282 | 28 | 36 | 2.E−12 | 50 | 32 | 45 | 5.E−16 |
| KRT23 | 1163 | 2190 | 887 | 1696 | 35 | 33 | 1.E−07 | 63 | 26 | 49 | 7.E−10 |

Example 11

Identification of Markers for Colon Cancer

The process of identification of MRD markers described above for neuroblastoma was applied to colon cancer, with the following filters/parameters applied:

Affymetrix U133: 88 tumors (20 lung metastases, 20 liver metastases), 10 normal PB samples;

Genes with tumor to PB gene expression signal ratio>30, cell line to PB gene expression signal ratio>9;

ttest $p<4\times10^{-7}$;

The following genes are excluded: of ubiquitous nature (e.g. collagen), with pseudogenes, BM expression by electronic northern or SAGE, median expression level (all tumors)<1000, and median expression level (metastatic tumors)<1000.

MRD markers thus identified for colon cancer are listed in Table 13, below:

| | median mets | liver mets | lung mets | median primary | mean PB | mets to PB | mets ttest | liver mets to PB | lung mets to PB | primary to PB | primary ttest |
|---|---|---|---|---|---|---|---|---|---|---|---|
| FABP1 | 4436 | 6245 | 3252 | 3081 | 13 | 348 | 2.E−08 | 491 | 255 | 242 | 1.E−08 |
| FXYD3 | 4858 | 5401 | 3899 | 4897 | 32 | 154 | 3.E−11 | 171 | 123 | 155 | 1.E−16 |
| TACSTD1 | 10370 | 10722 | 10293 | 8020 | 68 | 152 | 1.E−24 | 157 | 151 | 117 | 1.E−34 |
| CDH1 | 5987 | 6203 | 5978 | 5741 | 47 | 128 | 1.E−19 | 133 | 128 | 123 | 9.E−31 |
| CEACAM5 | 25918 | 24386 | 26392 | 18860 | 323 | 80 | 3.E−22 | 76 | 82 | 58 | 2.E−23 |
| kindlin 1 | 3636 | 4881 | 2643 | 2844 | 50 | 73 | 5.E−11 | 98 | 53 | 57 | 3.E−17 |
| LUM | 2042 | 1565 | 3960 | 2965 | 36 | 57 | 6.E−11 | 44 | 111 | 83 | 3.E−17 |
| KRT20 | 3062 | 3603 | 2883 | 3308 | 60 | 51 | 2.E−11 | 60 | 48 | 55 | 9.E−14 |
| AGR2 | 4464 | 5565 | 3955 | 6959 | 90 | 49 | 4.E−14 | 62 | 44 | 77 | 1.E−16 |
| RAI3 | 2693 | 3421 | 2288 | 2729 | 55 | 49 | 5.E−12 | 63 | 42 | 50 | 1.E−15 |
| MGP | 2440 | 1365 | 3849 | 1173 | 54 | 45 | 4.E−10 | 25 | 71 | 22 | 5.E−06 |
| LGALS4 | 7705 | 7894 | 7274 | 8978 | 182 | 42 | 2.E−18 | 43 | 40 | 49 | 5.E−25 |
| CLDN3 | 1985 | 2097 | 1974 | 2230 | 31 | 64 | 2.E−13 | 68 | 64 | 72 | 1.E−19 |
| MET | 1695 | 1769 | 1432 | 1587 | 27 | 63 | 3.E−17 | 66 | 53 | 59 | 2.E−22 |
| SCNN1A | 1965 | 2150 | 1594 | 2526 | 40 | 50 | 2.E−10 | 54 | 40 | 64 | 3.E−15 |
| TM4SF6 | 1816 | 1996 | 1746 | 1802 | 43 | 43 | 4.E−17 | 47 | 41 | 42 | 4.E−18 |
| THBS1 | 1005 | 979 | 1018 | 823 | 25 | 41 | 6.E−16 | 40 | 41 | 33 | 1.E−15 |
| CCL20 | 1068 | 1091 | 1051 | 1645 | 27 | 39 | 3.E−07 | 40 | 39 | 61 | 3.E−08 |
| IGFBP5 | 1787 | 776 | 3413 | 2610 | 46 | 39 | 3.E−08 | 17 | 74 | 56 | 2.E−10 |
| PLOD2 | 1638 | 1638 | 1605 | 1175 | 45 | 36 | 8.E−15 | 36 | 36 | 26 | 2.E−19 |
| PHLDA2 | 1029 | 1417 | 897 | 1282 | 28 | 36 | 2.E−12 | 50 | 32 | 45 | 5.E−16 |
| KRT23 | 1163 | 2190 | 887 | 1696 | 35 | 33 | 1.E−07 | 63 | 28 | 49 | 7.E−10 |

Example 12

Identification of Markers for Non-Small Cell Lung Carcinoma

Patients with non-small cell lung carcinoma (NSCLC) are often told that they have "no evidence of disease" after initial therapy. Yet it is crucial for these "cured" patients to have careful follow-up and monitoring for recurrence. Unfortunately, by the time such recurrence is detected by scan or symptoms, it is often too late for curative intervention. Targeting subclinical NSCLC is a logical alternative to the traditional approach of waiting for signs or symptoms of gross disease. Instead of the "killing paradigm", the alternative strategy of "regulatory control" is highly relevant in today's cancer management (Schipper, H., et al. 1995 *J Clin Oncol* 13:801-7). New classes of agents such as angiogenesis inhibitors, growth modulators or vaccines may not result in rapid tumor shrinkage. For these agents, since the maximum tolerated dose may not be the optimal biologic dose, the typical Phase I endpoint of toxicity is also inappropriate. Yet, detecting MRD has been a continuing challenge. Few markers are available for clinical validation. Given the inherent heterogeneity of NSCLC, a single marker is unlikely to be enough for detecting all CTC.

The process of identification of MRD markers described above for neuroblastoma was applied to non-small cell lung carcinoma, with the following filters/parameters applied:

Affymetrix U133: 115 tumors (9 metastatic), 10 normal PB samples;

Genes with tumor to PB gene expression signal ratio>20; ttest $p<10^{-8}$;

The following genes are excluded: of ubiquitous nature (e.g. collagen), with pseudogenes, BM expression by electronic northern or SAGE, and median expression level<2,000 units.

MRD markers thus identified for non-small cell lung carcinoma (mskcc) are listed in Table 14, below:

TABLE 14

| Gene Sy | median all tumor | median mets | mean PB | all tumor to PB | all tumor ttest | mets to PB |
|---|---|---|---|---|---|---|
| SFTPB | 17224 | 14515 | 103 | 168 | 1.E-31 | 141 |
| SFTPA2 | 12825 | 1612 | 83 | 155 | 3.E-22 | 20 |
| TACSTD | 5033 | 7013 | 64 | 78 | 5.E-53 | 109 |
| AGR2 | 5284 | 4568 | 86 | 61 | 9.E-26 | 53 |
| MGP | 3994 | 2673 | 74 | 54 | 5.E-25 | 36 |
| TACSTD | 6156 | 3632 | 130 | 48 | 6.E-37 | 28 |
| TITF1 | 2564 | 1669 | 57 | 45 | 1.E-35 | 29 |
| SCNN1A | 4210 | 8148 | 123 | 34 | 3.E-28 | 66 |

Example 13

Identification of Markers for Rhabdomyosarcoma

The process of identification of MRD markers described above for neuroblastoma was applied to Rhabdomyosarcoma, with the following filters/parameters applied:

Affymetrix U133: 23 alveolar RMS, 15 embryonal RMS, 10 normal PB samples;

Genes with tumor to PB gene expression signal ratio>20;

ttest $p<5\times10^{-7}$ for both alveolar and embryonal;

The following genes are excluded: of ubiquitous nature (e.g. collagen), with pseudogenes, BM expression by electronic northern or SAGE, and expression level of <1,000 units.

MRD markers thus identified for Rhabdomyosarcoma are listed in Table 15, below:

TABLE 15

| Gene Symbol | median all tumor | median PAX | median ERMS | All tumor to PB | All tumor ttest | Alveolar to PB | Alveolar ttest | ERMS to PB | ERMS ttest |
|---|---|---|---|---|---|---|---|---|---|
| CAPN6 | 5309 | 6922 | 936 | 152 | 5.E-08 | 198 | 1.E-07 | 27 | 6.E-03 |
| LUM | 3561 | 4721 | 2573 | 100 | 6.E-11 | 132 | 6.E-08 | 72 | 3.E-04 |
| MEG3 | 7774 | 11602 | 1362 | 84 | 3.E-08 | 126 | 1.E-08 | 15 | 3.E-03 |
| PEG3 | 10523 | 11919 | 4379 | 52 | 2.E-11 | 59 | 1.E-10 | 22 | 6.E-04 |
| OSF-2 | 9090 | 9899 | 7707 | 52 | 1.E-10 | 57 | 8.E-08 | 44 | 5.E-04 |
| ACTC | 14107 | 18798 | 7226 | 42 | 7.E-12 | 56 | 4.E-11 | 21 | 2.E-03 |
| TM4SF10 | 2303 | 2809 | 957 | 40 | 4.E-11 | 49 | 1.E-09 | 17 | 7.E-04 |
| MYOD1 | 1741 | 2789 | 865 | 52 | 3.E-10 | 83 | 5.E-09 | 26 | 1.E-04 |
| MET | 1080 | 1744 | 419 | 40 | 7.E-10 | 65 | 4.E-08 | 16 | 8.E-04 |
| RYR1 | 1775 | 3142 | 644 | 22 | 2.E-07 | 40 | 3.E-07 | 8 | 5.E-04 |
| SEPT10 | 1169 | 1190 | 1148 | 30 | 2.E-20 | 31 | 9.E-16 | 30 | 9.E-07 |
| ABAT | 1975 | 2575 | 320 | 23 | 2.E-07 | 30 | 4.E-08 | 4 | 3.E-03 |

Example 14

Identification of Markers for Soft Tissue Sarcoma

The process of identification of MRD markers described above for neuroblastoma was applied to soft tissue sarcoma, with the following filters/parameters applied:

Affymetrix U95: 52 tumors, 9 remission BM, 19 normal PB samples;

Genes with tumor to BM gene expression signal ratio>30; genes with tumor to PB gene expression signal ratio>5;

ttest $p<4\times10^{-6}$;

The following genes are excluded: of ubiquitous nature (e.g. collagen), with pseudogenes, BM expression by electronic northern or SAGE, and median expression level<350 units.

MRD markers thus identified for soft tissue sarcoma are listed in Table 16, below:

TABLE 16

| Gene Symbol | Median | | Mean | | all tumor | | | | mets | |
|---|---|---|---|---|---|---|---|---|---|---|
| | all tumor | Mets | BM | PB | to BM | ttest (BM) | to PB | ttest (PB) | to BM | to PB |
| TUSC3 | 371 | 473 | 6 | 79 | 60 | 6.E−11 | 5 | 9.E−09 | 76 | 6 |
| CPE | 1325 | 1067 | 22 | 102 | 59 | 5.E−08 | 13 | 1.E−07 | 48 | 10 |
| PDZRN3 | 370 | 292 | 7 | 82 | 55 | 3.E−10 | 5 | 9.E−08 | 43 | 4 |
| PTGIS | 755 | 657 | 15 | 143 | 52 | 3.E−06 | 5 | 2.E−05 | 45 | 5 |
| PMX1 | 751 | 799 | 18 | 149 | 43 | 5.E−08 | 5 | 1.E−06 | 45 | 5 |
| SEPT10 | 1448 | 1425 | 36 | 158 | 40 | 2.E−20 | 9 | 9.E−20 | 40 | 9 |
| TWIST | 514 | 559 | 17 | 63 | 31 | 2.E−09 | 8 | 1.E−08 | 33 | 9 |

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject having minimum residual disease (MRD) or a metastatic tumor, the method comprising:
   (a) isolating and amplifying mRNA from a peripheral blood or bone marrow sample from a subject who has previously undergone cancer treatment for neuroblastoma, and contacting said mRNA or cDNA thereof with an array consisting of oligonucleotide probes, each of said probes being hybridizable to one of genes CCND1, GD2 synthase, STMN2, CHGB, MAB21L1, DPYSL3, PGP9.5, KIF5C, GAP43, CRMP1, L1CAM, SCG2, ISL1, PHOX2B, RTN1, NP25, MAOA, AF1Q, NPY, RBP1, DDC, RGS5, PFN2, TH, ELAVL4, KIF21A, MAP2, KIF1A, MEG3, PCSK1N, GABRB3, GRIA2, SOX11, IDAX, and CNTFR, wherein an elevated level of mRNA of at least three of said genes including CCND1 and GD2 synthase compared to the levels for the same genes in normal peripheral blood or bone marrow samples identifies the subject as having MRD or a metastatic tumor; and
   (b) administering treatment to the subject identified as having MRD or a metastatic tumor.

2. The method of claim 1, wherein the elevated level of mRNA of the at least three genes is at least 2 standard deviations (SD) above a mean expression level of the genes in normal blood or bone marrow samples.

3. The method of claim 1, wherein the treatment is selected from the group consisting of chemotherapy, radiation, immunotherapy, and targeted therapy using small molecules.

4. The method of claim 1, further comprising repeating said method one or more times until the subject is no longer identified as having MRD or a metastatic tumor.

5. The method of claim 1, wherein the at least three genes include CCND1, GD2 synthase and ISL1 or CCDN1, GD2 synthase and PHOX2B.

6. The method of claim 1, wherein the at least three genes include CCND1, GD2 synthase, ISL1 and PHOX2B.

7. The method of claim 1, wherein the treatment is administration of anti-GD2 monoclonal antibody 3F8 plus granulocyte-macrophage colony stimulating factor (GM-CSF).

8. A method of detecting a metastatic neuroblastoma tumor cell in a blood or bone marrow sample from a subject comprising:
   isolating and amplifying mRNA from a peripheral blood or bone marrow sample from the subject and contacting said mRNA or cDNA thereof with an array consisting of oligonucleotide probes, each of said probes being hybridizable to one of genes CCND1, GD2 synthase, STMN2, CHGB, MAB21L1, DPYSL3, PGP9.5, KIF5C, GAP43, CRMP1, L1CAM, SCG2, ISL1, PHOX2B, RTN1, NP25, MAOA, AF1Q, NPY, RBP1, DDC, RGS5, PFN2, TH, ELAVL4, KIF21A, MAP2, KIF1A, MEG3, PCSK1N, GABRB3, GRIA2, SOX11, IDAX, and CNTFR, wherein an elevated level of mRNA of at least three of said genes including CCND1 and GD2 synthase in said sample compared to mRNA levels for the same genes in normal peripheral blood or bone marrow samples indicates the presence of a metastatic tumor cell.

9. A method of identifying a subject with minimum residual disease (MRD) or a metastatic tumor comprising:
   isolating and amplifying mRNA from a peripheral blood or bone marrow sample from a subject who has previously undergone cancer treatment for neuroblastoma and contacting said mRNA or a-cDNA thereof with an array consisting of oligonucleotide probes, each of said probes being hybridizable to one of genes CCND1, GD2 synthase, STMN2, CHGB, MAB21L1, DPYSL3, PGP9.5, KIF5C, GAP43, CRMP1, L1CAM, SCG2, ISL1, PHOX2B, RTN1, NP25, MAOA, AF1Q, NPY, RBP1, DDC, RGS5, PFN2, TH, ELAVL4, KIF21A, MAP2, KIF1A, MEG3, PCSK1N, GABRB3, GRIA2, SOX11, IDAX, and CNTFR, wherein an elevated level of mRNA of at least three of said genes including CCND1 and GD2 synthase in said sample compared to mRNA levels for the same genes in normal peripheral blood or bone marrow samples identifies the subject as having MRD or a metastatic tumor.

10. The method of claim 9, wherein the at least three genes include CCND1, GD2 synthase and ISL1.

11. The method of claim 9, wherein the at least three genes include CCND1, GD2 synthase and PHOX2B.

* * * * *